United States Patent [19]

Masukawa et al.

[11] Patent Number: 4,840,883

[45] Date of Patent: Jun. 20, 1989

[54] LIGHT-SENSITIVE SILVER HALIDE COLOR PHOTOGRAPHIC MATERIAL CONTAINING NOVEL CYAN COUPLER

[75] Inventors: Toyoaki Masukawa; Hidetaka Ninomiya; Hiroyuki Iizuka, all of Hino, Japan

[73] Assignee: Konica Corporation, Tokyo, Japan

[21] Appl. No.: 206,580

[22] Filed: Jun. 14, 1988

[30] Foreign Application Priority Data

Jun. 26, 1987 [JP] Japan ............................ 62-160324

[51] Int. Cl.$^4$ ............................................. G03C 7/34
[52] U.S. Cl. ...................................... 430/553; 430/552
[58] Field of Search ............................... 430/552, 553

[56] References Cited

U.S. PATENT DOCUMENTS

| | | | |
|---|---|---|---|
| 3,311,476 | 3/1967 | Loria | 430/553 |
| 4,513,081 | 4/1985 | Okazaki et al. | 430/553 |
| 4,621,047 | 11/1986 | Kishimoto et al. | 430/553 |
| 4,696,893 | 9/1987 | Umemoto et al. | 430/552 |

*Primary Examiner*—Richard L. Schilling
*Attorney, Agent, or Firm*—Frishauf, Holtz, Goodman & Woodward

[57] ABSTRACT

There is disclosed a light-sensitive silver halide color photographic material containing novel cyan coupler which comprises a light-sensitive silver halide color photographic material having at least one silver halide emulsion layer on a support, characterized in that at least one layer of the silver halide emulsion layer contains at least one cyan coupler represented by the formula (I) shown below:

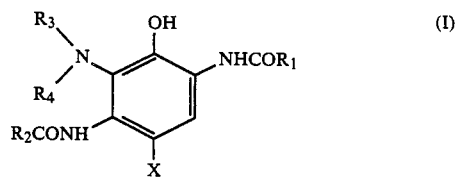

wherein $R_1$ and $R_2$ each represent an alkyl group, an aryl group, a heterocyclic group, a dialkylamino group, an anilino group, an alkoxy group or an aryloxy group; $R_3$ represents a hydrogen atom or an alkyl group; $R_4$ represents a hydrogen atom, an alkyl group, an aryl group, A $R_5CO$—group or a $R_5SO_2$—group; provided that $R_3$ and $R_4$ cannot be hydrogen atoms at the same time; $R_5$ represents a hydrogen atom, an alkyl group, an aryl group, a dialkylamino group, an anilino group, an alkoxy group or an aryloxy group; and X represents a hydrogen atom or an eliminatable group through the reaction with the oxidized product of a color developing agent.

22 Claims, No Drawings

LIGHT-SENSITIVE SILVER HALIDE COLOR PHOTOGRAPHIC MATERIAL CONTAINING NOVEL CYAN COUPLER

BACKGROUND OF THE INVENTION

This invention relates to a light-sensitive silver halide color photographic material containing a novel cyan coupler.

By carrying out color developing processing of a light-sensitive silver halide color photographic material after giving exposure thereto, an aromatic primary amine developing agent reacts with a dye forming coupler (hereinafter merely called "coupler") to form a color image. In this method, color reproduction according to the subtractive color photography is effected, whereby yellow, magenta and cyan color images in complementary color relationships with blue, green and red, respectively, are formed.

As the cyan coupler, generally phenols or naphthols have been widely used, but the cyan coupler selected from phenols and naphthols of the prior art had some problems to be solved. For example, the color images obtained from 2,5-diacylaminophenol type cyan couplers as described in U.S. Pat. No. 2,367,531, No. 2,369,929, No. 2,423,730, No. 2,801,171, etc. are generally inferior in heat fastness, while the acylaminophenol type cyan couplers as described in U.S. Pat. No. 2,772,162, No. 2,895,826, etc. had the drawback that the light fastness of the color image obtained was generally bad. Also, 1-hydroxy-2-naphthoamide type cyan couplers are also insufficient in both light and heat (particularly humid heat) fastness.

SUMMARY OF THE INVENTION

Accordingly, an object of the present invention is to provide a novel cyan coupler which improves the drawbacks of the cyan couplers of the prior art and further gives a dye image which can stand storage for a long term. Another object of the present invention is to provide a light-sensitive silver halide color photographic material having at least one silver halide emulsion layer containing such a coupler.

The above objects of the present invention have been accomplished by a light-sensitive silver halide color photographic material having at least one silver halide emulsion layer on a support, characterized in that at least one layer of said silver halide emulsion layer contains at least one cyan coupler represented by the formula (I) shown below:

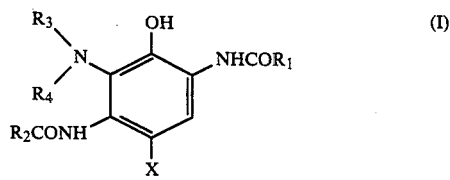

wherein $R_1$ and $R_2$ each represent an alkyl group, an aryl group, a heterocyclic group, a dialkylamino group, an anilino group, an alkoxy group or an arloxy group; $R_3$ represents a hydrogen atom or an alkyl group; $R_4$ represents a hydrogen atom, an alkyl group, an aryl group, a $R_5CO$— group or a $R_5SO_2$— group; provided that $R_3$ and $R_4$ cannot be hydrogen atoms at the same time; $R_5$ represents a hydrogen atom, an alkyl group, an aryl group, a dialkylamino group, an anilino group, an alkoxy group or an aryloxy group; and X represents a hydrogen atom or an eliminatable group through the reaction with the oxidized product of a color developing agent.

DESCRIPTION OF THE PREFERRED EMBODIMENTS

In the above formula (I), the alkyl group represented by $R_1$ and $R_2$ may be either straight chain, branched or cyclic, and includes those having substituents. Specific examples may include groups of methyl, ethyl, iso-propyl, t-butyl, cyclohexyl, undecyl, trifluoromethyl, trichloromethyl, perfluoropropyl, 2-methoxyethyl, hyroxymethyl, benzyl, phenethyl, 3-(2,5-di-t-amylphenoxy)-propyl, 1-(4-butanesulfonamidophenoxy)tridecyl, 1-(2,4,6-trichlorophenoxy)-undecyl, and other groups. Among them, halosubstituted alkyl groups, subtituted aryloxy-substituted alkyl groups are preferred.

The aryl group represented by $R_1$ and $R_2$ includes also those having substituents, and preferable substituents may include halogen atoms, and each groups of alkyl, aryl, heterocyclic, alkoxy, aryloxy, acyl, ester, amide, imide, ureido, sulfonyl, alkoxycarbonyl, aryloxycarbonyl, hydroxy, carboxy, sulfo, cyano, nitro, etc.

Examples of the heterocyclic group represented by $R_1$ and $R_2$ may include 2-furyl, 2-imidazolyl, 2-thienyl, 2-pyridyl, 6-quinolyl and the like.

The dialkylamino group represented by $R_1$ and $R_2$ may be preferably an unsubstituted dialkylamino group, as exemplified by dimethylamino, diethylamino, methylbutylamino groups, etc.

The anilino group may have also substituents, and anilino groups substituted with, for example, halogen atoms, alkyl, alkoxy, amide, sulfonamide, cyano, nitro groups, etc. are preferred.

As the alkoxy group, preferred are non-substituted alkoxy groups such as methoxy, ethoxy, butoxy, octyloxy, dodecyloxy and the like, and also as the aryloxy group, preferred are non-substituted ones such as phenoxy group.

As the alkyl group represented by $R_3$ and $R_4$, substituted or unsubstituted alkyl groups having 1 to 22 carbon atoms may be included, preferably unsubstituted alkyl groups.

As the aryl group represented by $R_4$, the same aryl groups as mentioned for $R_1$ and $R_2$ can be included.

The alkyl, aryl, dialkylamino, anilino, alkoxy and aryloxy groups represented by $R_5$ have the same meanings as already mentioned for $R_1$ and $R_2$.

Among the groups represented by $R_3$ and $R_4$, the cases wherein $R_3$ is a hydrogen atom or a lower alkyl group and $R_4$ is an alkylcarbonyl or arylcarbonyl group ($R_5CO$—), an alkylsulfonyl or arylsulfonyl group ($R_5SO_2$—) are preferred.

As the group represented by X eliminatable by the reaction with the oxidized product of a color developing agent, the so-called split-off group conventionally used in the field of the art may be included.

Among the cyan couplers represented by the formula (I), preferred are those as shown by the following formulae (II), (III) and (IV):

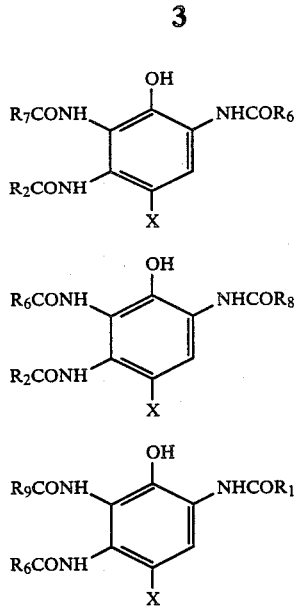

In the above formulae (II) to (IV), $R_1$, $R_2$ and X have the same meanings as $R_1$, $R_2$ and X in the formula (I), respectively. $R_6$ represents an alkyl group substituted by at least one halogen atom, $R_7$ represents a substituted or unsubstituted amino group, an alkoxy group or an aryloxy group, $R_8$ represents a substituted or unsubstituted phenyl group, and $R_9$ represents a substituted or unsubstituted amino group, alkoxy group, alkyl group or aryl group.

Next, each compound is explained in more detail.

As $R_2$ in the formula (II), preferred are a substituted or unsubstituted alkyl group, phenyl group or anilino group, more preferably a substituted alkyl group, particularly preferably an alkoxy group, a phenoxy group, an alkylsulfonyl group or a phenylsulfonyl-substituted alkyl group.

As $R_6$, preferred are an alkyl group substituted by a chlorine atom or a bromine atom, more preferred are an alkyl group of which all the hydrogen atoms are substituted by chlorine atoms and/or fluorine atoms, particularly a perfluoroalkyl group is preferred.

As $R_7$, preferred is an anilino group.

As X, preferred are a hydrogen atom, a chlorine atom, a substituted or unsubstituted alkoxy group and aryloxy group, and more preferably a chlorine atom, a substituted alkoxy group and a substituted aryloxy group.

As $R_2$, $R_6$ and X in the formula (III), preferred substituents may be mentioned those as specifically mentioned in the formula (II), respectively.

As $R_8$, preferred is an unsubstituted phenyl group or a phenyl group substituted by a halogen atom, an alkoxy group or an acylamino group.

As $R_1$ in the formula (IV), preferred are a substituted or unsubstituted alkyl group, a phenyl group and an anilino group, more preferably a substituted alkyl group.

As $R_6$ and X, preferred substituents may be mentioned those as specifically mentioned in the formula (III), respectively.

As $R_9$, preferred are a substituted or unsubstituted alkyl group, alkoxy group, aryl group and anilino group, and more preferably a substituted alkyl group.

Representative specific examples of the novel cyan coupler to be used in the present invention (called the cyan coupler of the present invention) are enumerated below, but the present invention is not limited to these.

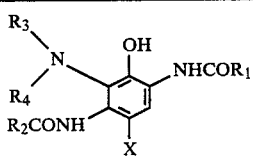

| No. | $R_1$ | $R_2$ | $R_3$ | $R_4$ | X |
|---|---|---|---|---|---|
| I-1 | ![pentafluorophenyl] | $-CHO-\text{(2-}C_5H_{11}(t)\text{, 4-}C_5H_{11}(t)\text{-phenyl)}$ with $C_3H_7(i)$ | H | $-COCH_3$ | Cl |
| I-2 | 3-Cl-phenyl | $-CHO-\text{(2-}C_5H_{11}(t)\text{, 4-}C_5H_{11}(t)\text{-phenyl)}$ with $C_4H_9$ | H | $-COC_2H_5$ | Cl |
| I-3 | 4-CN-phenyl | $-CHO-\text{(4-}NHSO_2C_4H_9\text{-phenyl)}$ with $C_{12}H_{25}$ | H | $-CO-\text{phenyl}$ | Cl |
| I-4 | $-C_3F_7$ | $-CHO-\text{(2-}C_5H_{11}(t)\text{, 4-}C_5H_{11}(t)\text{-phenyl)}$ with $C_4H_9$ | H | $-COC_3H_7$ | H |

-continued

| No. | R6 | R2 | R7 | X |
|---|---|---|---|---|
| I-5 | $-C_2F_5$ | 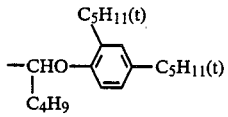 -CHO- with $C_5H_{11}(t)$, $C_5H_{11}(t)$, $C_4H_9$ | H | $-COCH_3$ | H |
| I-6 |  (phenyl) | 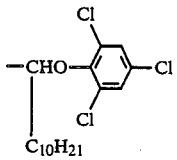 -CHO- with 2,4,6-Cl3, $C_{10}H_{21}$ | H | $-CO-$ (2-chlorophenyl) | Cl |
| I-7 | $-C_4H_9(t)$ | 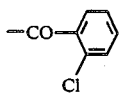 (methyl, CN, Cl phenyl) | H | $-SO_2C_4H_9$ | Cl |
| I-8 | $-(CF_2)_4H$ | 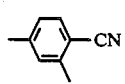 -CHO- with $C_5H_{11}(t)$, $C_5H_{11}(t)$, $C_4H_9$ | H | $-SO_2-$ (phenyl) | H |
| I-9 | 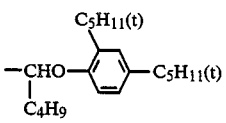 $-NH-$ (CN, Cl phenyl) | 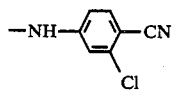 -CHO- with $C_5H_{11}(t)$, $C_5H_{11}(t)$, $C_4H_9$ | H | $-COC_3H_7$ | H |
| I-10 | 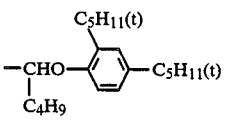 $-NH-$ (CN, Cl phenyl) | 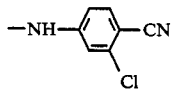 -CHO- with $C_5H_{11}(t)$, $C_5H_{11}(t)$, $C_4H_9$ | H | $-COC_3H_7$ | $-OCH_2COCOOC_2H_5$ |
| I-11 | 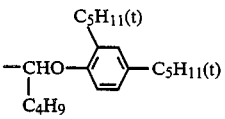 $-NH-$ (CN, Cl phenyl) | 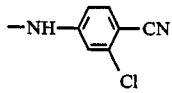 -CHO- with $C_5H_{11}(t)$, $C_5H_{11}(t)$, $C_4H_9$ | H | $-COC_3H_7$ | 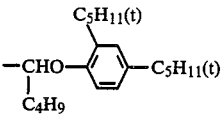 $-O-$ (phenyl) $-OCH_3$ |

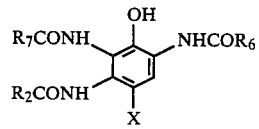

| No. | R6 | R2 | R7 | X |
|---|---|---|---|---|
| II-1 | $-(CF_2)_3OH$ | $-CH_3$ | 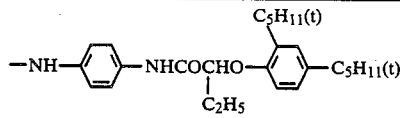 $-NH-$ (phenyl) $-NHCOCHO-$ with $C_5H_{11}(t)$, $C_5H_{11}(t)$, $C_2H_5$ | $-Cl$ |
| II-2 | $-CF_3$ | $-C_{12}H_{25}$ | $-OC_4H_9(i)$ | $-Cl$ |
| II-3 | $-CCl_3$ | 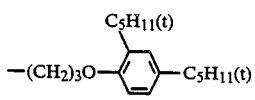 $-(CH_2)_3O-$ with $C_5H_{11}(t)$, $C_5H_{11}(t)$ | 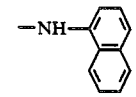 $-NH-$ (naphthyl) | $-H$ |
| II-4 | $-C_2F_5$ | 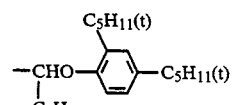 $-CHO-$ with $C_5H_{11}(t)$, $C_5H_{11}(t)$, $C_2H_5$ | 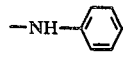 $-NH-$ (phenyl) | $-Cl$ |
| II-5 | $-C_2F_5$ | 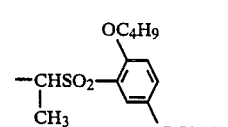 $-CHSO_2-$ with $OC_4H_9$, $C_8H_{17}(t)$, $CH_3$ | 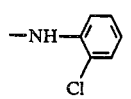 $-NH-$ (Cl phenyl) | $-O-$ (phenyl) $-NHCO(CH_2)_2COOH$ |

-continued

| No. | | | | |
|---|---|---|---|---|
| II-6 | —C₃F₇ | —CHO-(2,5-dichlorophenyl), C₁₂H₂₅ | —NH-(benzodioxole) | —Cl |
| II-7 | —C₃F₇ | —CHO-(2,4-di-t-C₅H₁₁-phenyl), C₄H₉ | —NH-(2,6-dichlorophenyl) | —Cl |
| II-8 | —C₄F₉ | —CH₂CH₂OCH₃ | —NH-C₆H₄-NHCOC₁₂H₂₅ | —Cl |
| II-9 | —(CF₂)₄H | —C₁₂H₂₅ | —NH-(2-methoxyphenyl) | —OCH₂CONH(CH₂)₂OCH₃ |
| II-10 | —C₇H₁₅ | —CH₂CH₂SO₂C₁₂H₂₅ | —NH-(4-chloro-3-cyanophenyl) | —Cl |

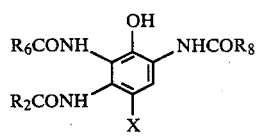

| No. | R₈ | R₂ | R₆ | X |
|---|---|---|---|---|
| III-1 | —C₆H₄-NHCOCHO-(2,4-di-t-C₅H₁₁-phenyl), C₄H₉ | —C₆H₅ | —CF₃ | H |
| III-2 | —C₆H₄-CN | —C₁₂H₂₅ | —CCl₃ | —OCH₂CH₂SCHC₁₂H₂₅ COOH |
| III-3 | —(2,4,5-trichlorophenyl) | —CH₂CH₂SO₂C₁₂H₂₅ | —CHCl₂ | —O-C₆H₄-C₈H₁₇(t) |
| III-4 | —C₆H₅ | —CHO-(2,4-di-t-C₅H₁₁-phenyl), C₂H₅ | —C₂F₅ | —Cl |
| III-5 | —C₆F₅ | —CHO-(2,4-di-t-C₅H₁₁-phenyl), C₃H₇(i) | —C₂F₅ | —Cl |
| III-6 | —(2-chlorophenyl) | —CHO-(4-t-C₅H₁₁-phenyl), C₂H₅ with C₅H₁₁(t) | —C₃F₇ | —OCH₂COOC₂H₅ |

-continued
| No. | | | | |
|---|---|---|---|---|
| III-7 | 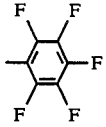 | 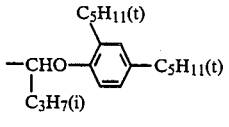 | —C₃F₇ | 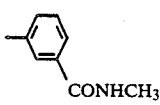 |
| III-8 | 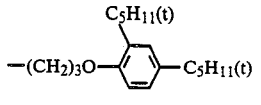 | 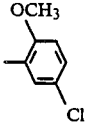 | —C₄F₉ | —Cl |
| III-9 | 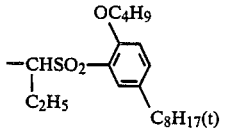 | 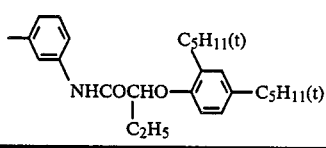 | —(CF₂)₄H | —OCH₂CONH(CH₂)₂OCH₃ |
| III-10 | 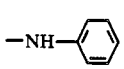 | —NH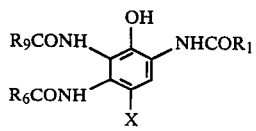 | —C₅F₁₁ | —Cl |
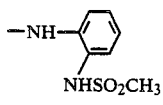
| No. | $R_1$ | $R_6$ | $R_9$ | X |
|---|---|---|---|---|
| IV-1 | —C₁₂H₂₅ | —CF₃ | —OC₄H₉(i) | —Cl |
| IV-2 | —CH₂CH₂SO₂C₁₂H₂₅ | —CCl₃ | 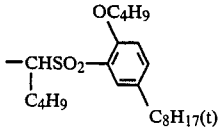 | H |
| IV-3 |  | —CHCl₂ | 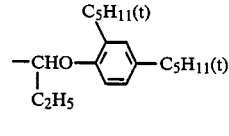 | —Cl |
| IV-4 | 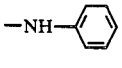 | —C₂F₅ | 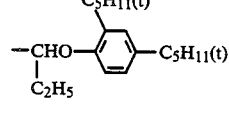 | —Cl |
| IV-5 | 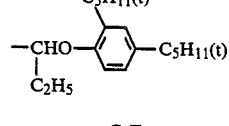 | —C₂F₅ | —C₂F₅ | —Cl |
| IV-6 | 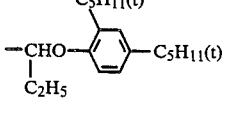 | —C₃F₇ | —C₃F₇ | —Cl |
| IV-7 | —C₃F₇ | —C₃F₇ |  | 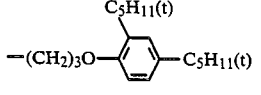 |
| IV-8 | 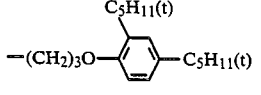 | —C₄H₉ | | —OCH₂CONH(CH₂)₂OCH₃ |

| | | | | |
|---|---|---|---|---|
| IV-9 | 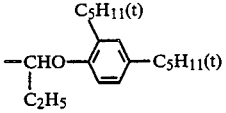 | $-(CF_2)_4H$ | $-CH_3$ | $-Cl$ |
| IV-10 | 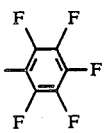 | $-C_5F_{11}$ | $-C_{12}H_{25}$ | $-OCH_2SCHC_{12}H_{25}$<br>$\quad\quad\quad\quad\quad\mid$<br>$\quad\quad\quad\quad\;\;COOH$ |

In the following, synthesis examples of the cyan coupler of the present invention are shown.

Synthesis example 1 (synthesis of the exemplary compound I—1)

Synthesis of 2-pentafluorobenzamido-4-chloro-5-{2-(2,4-di-t-amylphenoxy)-3-methylbutaneamido}-6-nitrophenol An amount of 5 g ($7.3 \times 10^{-3}$ mole) of 2-pentafluorobenzamido-4-chloro-5-{2-(2,4-di-t-amylphenoxy)-3-methylbutaneamido}phenol was dissolved in 25 ml of acetone and 25 ml of acetic acid, and cooled in a salt-ice bath. To this solution was added dropwise 0.55 ml (one equivalent) of a 61% nitric acid (specific gravity: 1.38) diluted with 2 ml of acetic acid slowly so that the liquid temperature might not exceed 3° C. Further, the mixture was cooled to $-5°$ C. and after addition of 0.3 ml of conc. sulfuric acid, the mixture was gradually returned to room temperature (the solution became colored in orange). The reaction mixture was poured into water, and the yellow solids precipitated were filtered and washed with water. The crude product (5.1 g) was used as such for the subsequent reaction.

Synthesis of 2-pentafluorobenzamido-4-chloro-5-{2-(2,4-di-t-amylphenoxy)-3-methylbutaneamido}-6-aminophenol The above nitro derivative (4.1 g, $5.7 \times 10^{-3}$ mole) was dissolved in 100 ml of ethanol and 2 ml (tetra equivalents) of conc. hydrochloric acid was added thereto. Hydrogenation was effected with the use of 0.4 g of Pd-C (palladium-carbon) as the catalyst. The color of the nitro derivative disappeared in 2 hours, and the Pd-C was removed by filtration and ethanol was evaporated from the filtrate, followed by extraction of the residue with ethyl acetate. The ethyl acetate layer was washed with an aqueous sodium hydrogen carbonate solution and then with water, and after drying over magnesium sulfate, ethyl acetate was evaporated. The residue was purified by separation according to column chromatography to give 3.1 g of an amorphous solid.

Synthesis of 2-pentafluorobenzamido-4-chloro-5-{2-(2,4-di-t-amylphenoxy)-3-methylbutaneamido}-6-acetamidophenol (Compound I—1)

The above amino derivative (1.01 g, $1.48 \times 10^{-3}$ mole) was dissolved in 10 ml of acetonitrile, and refluxed under heating with addition of 0.2 ml (1.3 equivalents) of acetic anhydride for 4 hours. The reaction mixture was applied to silica gel column chromatography (toluene→toluene/acetone=50/1) to separate the desired product, which was recrystallized from a solvent mixture of hexaneethanol (20/1) to give 0.64 g of the Compound I—1. melting point: 196° to 198° C.

Synthesis example 2 (synthesis of the exemplary compound II—4)

Synthesis of 2-pentafluoropropylamido-4-chloro-5-nitrophenol

In 100 ml of acetonitrile was dissolved 11 g ($58 \times 10^{-3}$ mole) of 2-amino-4-chloro-5-nitrophenol. To the solution was added 19.9 g of pentafluoropropionic acid anhydride at room temperature and then the mixture was heated under reflux for 2 hours. After the reaction, a solvent was evaporated under reduced pressure and the residue was recrystallized from hexane to obtain products. Yield: 17 g (87%).

Synthesis of 2-pentafluoropropylamido-4-chloro-5-aminophenol

In 150 ml of ethanol was dissolved 13.7 g ($41 \times 10^{-3}$ mole) of 2-pentafluoropropylamido-4-chloro-5-nitrophenol and hydrogenation was effected by using 0.9 g of Pd-C as a catalyst. The color of the nitro derivative disappeared in 2 hours, and the Pd-C was removed by filtration and ethanol was evaporated from the filtrate, followed by extraction of the residue with ethyl acetate. The ethyl acetate layer was washed with an aqueous sodium hydrogen carbonate solution and then with water, and after drying over magnesium sulfate, ethyl acetate was evaporated. 12.1 g of a crude product was used as such for the subsequent reaction.

Synthesis of 2-pentafluoropropylamido-4-chloro-5-{2-(2,4-di-t-amylphenoxy)butaneamido}phenol In 100 ml of ethyl acetate was dissolved 12 g ($39 \times 10^{-3}$ mole) of 2-pentafluoropropylamido-4-chloro-5-aminophenol and then 15 g ($43 \times 10^{-3}$ mole) of 2-(2,4-di-t-amylphenoxy)butanoic acid chloride and 3.5 g ($43 \times 10^{-3}$ mole) of pyridine were added to the solution, and the mixture was stirred at room temperature for 3 hours. After the reaction, a solvent was removed by evaporation, the residue was separated and purified through a column chromatography, and recrystallized from n-hexane to obtain the title compound. Yield: 9.0 g, FD-Mass 608, melting point: 167° to 168° C.

Synthesis of 2-pentafluoropropylamido-4-chloro-5-{2-(2,4-di-t-amylphenoxy)butanamido}-6-nitrophenol In 100 ml of acetic acid and 40 ml of dimethylformamide was dissolved 9 g ($15 \times 10^{-3}$ mole) of 2-pentafluoropropylamido-4-chloro-5-{2-(2,4-di-t-amylphenoxy)butanamido}phenol. To the solution was added dropwise slowly a solution of 1.2 g ($18 \times 10^{-3}$ mole) of sodium nitrite dissolved in 5 ml of a distilled water at room temperature, and then the mixture was stirred for one hour. The reaction mixture was poured into ice-cold water and precipitated yellow solids were collected by filtration and washed with water. Yield: 8 g.

Synthesis of 2-pentafluoropropylamido-4-chloro-5-{2-(2,4-di-t-amylphenoxy)butanamido}-6-aminophenol In 30 ml of tetrahydrofuran and 30 ml of ethanol was dissolved 8.3 g ($13 \times 10^{-3}$ mole) of 2-pentafluoropropylamido-4-chloro-5-{2-(2,4-di-t-amylphenoxy)butanamido}-6-nitrophenol and hydrogenation was effected by using 0.6 g of Pd-C as a catalyst. The color of the nitro derivative disappeared in 4 hours, and the Pd-C was removed by filtration and a solvent was evaporated therefrom under reduced pressure, followed by extraction of the residue with ethyl acetate. The ethyl acetate layer was washed with an aqueous sodium hydrogen carbonate solution and then with water, and after drying over magnesium sulfate, ethyl acetate was evaporated. Yield: 7.9 g.

Synthesis of phenyl-[2-{2-(2,4-di-t-amylphenoxy)butanamido}-3-chloro-5-pentafluoropropylamido-6-hydroxyphenyl-]urea In 100 ml of ethyl acetate was dissolved 3.6 g ($5.8 \times 10^{-3}$ mole) of 2-pentafluoropropylamido-4-chloro-5-{2-(2,4-di-t-amylphenoxy)butanamido}-6-aminophenol, and 0.69 g ($5.8 \times 10^{-3}$ mole) of phenylisocyanate was added to the solution and the mixture was refluxed under heating for 2 hours. After the reaction, a solvent was distilled off, and the residue was separated and purified through column chromatography and recrystallized from hexane. Yield: 2.4 g (60%), FD-Mass: 741, melting point: 127° to 128° C.

Synthesis example 3 (synthesis of the exemplary compound III—4)

Synthesis of 2-benzamido-4-chloro-5-nitrophenol

In 100 ml of ethyl acetate was dissolved 40 g ($210 \times 10^{-3}$ mole) of 2-amino-4-chloro-5-nitrophenol, and 33 g of benzoyl chloride was added at room temperature and then the mixture was refluxed under heating for 2 hours. After the reaction, a solvent was distilled off under reduced pressure and the residue was recrystallized from hexane to obtain products. Yield: 60 g.

Synthesis of 2-benzamido-4-chloro-5-aminophenol

In 100 ml of ethanol was dissolved 28 g ($96 \times 10^{-3}$ mole) of 2-benzamido-4-chloro-5-nitrophenol and hydrogenation was effected by using 1.5 g of Pd-C as a catalyst. The color of the nitro derivative disappeared in 2 hours, and the Pd-C was removed by filtration and ethanol was evaporated from the filtrate, followed by extraction of the residue with ethyl acetate. The ethyl acetate layer was washed with an aqueous sodium hydrogen carbonate solution and then with water, and after drying over magnesium sulfate, ethyl acetate was evaporated. 26 g of the crude product was used as such for the following reaction.

Synthesis of 2-benzamido-4-chloro-5-{2-(2,4-di-t-amylphenoxy)-butanamido}phenol In 100 of ethyl acetate was dissolved 15 g ($57 \times 10^{-3}$ mole) of 2-benzamido-4-chloro-5-aminophenol, and then 21 g of 2-(2,4-di-t-amylphenoxy)butanoic acid chloride and 5 g of pyridine were added thereto and the mixture was stirred at room temperature for 3 hours. After the reaction, a solvent was distilled off, and the residue was separated and purified through column chromatography and recrystallized from n-hexane to obtain the title compound. Yield: 14.1 g, FD-Mass: 564, melting point: 190° to 191° C.

synthesis of 2-nitro-3-{2-(2,4-di-t-amylphenoxy)butanamido}-4-chloro-6-benzamidophenol In 100 ml of acetic acid and 100 ml of dimethylformamide was dissolved 20 g ($35 \times 10^{-3}$ mole) of 2-benzamido-4-chloro-5-{2-(2,4-di-t-amylphenoxy)-butanamido}phenol. To the solution was added dropwise slowly a solution of 2.7 g of sodium nitrite dissolved in 5 ml of a distilled water at room temperature, and then the mixture was stirred for 2 hours. The reaction mixture was poured into ice-cold water, and precipitated yellow solids were collected by filtration and washed with water. Yield: 21 g.

Synthesis of 2-amino-3-{2-(2,4-di-t-amylphenoxy)butanamido}-4-chloro-6-benzamidophenol In 50 ml of tetrahydrofuran and 100 ml of ethanol was dissolved 21 g ($13 \times 10^{-3}$ mole) of 2-nitro-3-{2-(2,4-di-t-amylphenoxy)butanamido}-4-chloro-6-benzamidophenol and hydrogenation was effected by using 1.2 g of Pd-C as a catalyst. The color of the nitro derivative disappeared in 4 hours, and the Pd-C was removed by filtration and a solvent was evaporated therefrom under reduced pressure, followed by extraction of the residue with ethyl acetate. The ethyl acetate layer was washed with an aqueous sodium hydrogen carbonate solution and then with water, and after drying over magnesium sulfate, ethyl acetate was evaporated. Yield: 20 g.

Synthesis of 2-pentafluoropropylamido-3-{2-(2,4-di-t-amylphenoxy)butanamido}-4-chloro-6-benzaminophenol In 50 ml of ethyl acetate was dissolved 4 g ($6.9 \times 10^{-3}$ mole) of 2-amino-3-{2-(2,4-di-t-amylphenoxy)butanamido}-4-chloro-6-benzamindophenol, and 2.4 g of pentafluoropropionic acid anhydride was added to the solution and the mixture was stirred at room temperature for 2 hours. After the reaction, a solvent was evaporated and the residue was separated and purified through colomn chromatography and recrystallized from hexane. Yield: 1.8 g, FD-Mass: 724, melting point: 197° to 198° C.

Synthesis example 4 (synthesis of the exemplary compound IV—5)

Synthesis of 2-{2-(2,4-di-t-amylphenoxy)butanamido}-4-chloro-5-nitrophenol

In 100 ml of ethyl acetate was dissolved 25 g ($133 \times 10^{-3}$ mole) of 2-amino-4-chloro-5-nitrophenol. To the solution was added 50 g of 2-(2,4-di-t-amylphenoxy)butanoic acid chloride at room temperature, and then the mixture was refluxed under heating for 2 hours. After the reaction, a solvent was evaporated under reduced pressure and the residue was recrystallized from hexane to obtain products. Yield: 61 g.

Synthesis of 2-{2-(2,4-di-t-amylphenoxy)butanamido}-4-chloro-5-aminophenol

In 100 ml of ethanol was dissolved 30 g ($61 \times 10^{-3}$ mole) of 2-{2-(2,4-di-t-amylphenoxy)butanamido}-4-chloro-5-nitrophenol and hydrogenation was effected by using 1.5 g of Pd-C as a catalyst. The color of the nitro derivative disappeared in 2 hours, and the Pd-C was removed by filtration and ethanol was evaporated from the filtrate, followed by extraction of the residue with ethyl acetate. The ethyl acetate layer was washed with an aqueous sodium hydrogen carbonate solution and then with water, and after drying over magnesium sulfate, ethyl acetate was evaporated. 28 g of the crude product was used as such for the following reaction.

Synthesis of 2-{2-(2,4-di-t-amylphenoxy)butanamido}-4-chloro-5-pentafluoropropylamidophenol In 100 ml of ethyl acetate was dissolved 20 g ($43 \times 10^{-3}$ mole) of 2-{2-(2,4-di-t-amylphenoxy)butanamido}-4-chloro-5-aminophenol, and 15 g of pentafluoropropionic acid anhydride was added to the solution and the mixture was stirred at room temperature for 2 hours. After the reaction, a solvent was evaporated and the residue was separated and purified through column chromatography and recrystallized from n-hexane to obtain the title compound. Yield: 14 g, FD-Mass: 606, melting point: 175° to 176° C.

Synthesis of 2-nitro-3-pentafluoropropylamido-4-chloro-6-{2-(2,4-di-t-amylphenoxy)butanamino}phenol In 100 ml of acetic acid and 20 ml of dimethylformamide was dissolved 13.4 g ($22 \times 10^{-3}$ mole) of 2-{2-(2,4-di-t-amylphenoxy)butanamido}-4-chloro-5-pentafluoropropylamidophenol. To the solution was added dropwise slowly a solution of 1.7 g of sodium nitrite dissolved in 5 ml of distilled water at room temperature, and then the mixture was stirred for one hour. The reaction mixture was poured into ice-cold water and precipitated yellow solid was collected by filtration and washed with water. Yield: 13 g.

Synthesis of 2-amino-3-pentafluoropropylamido-4-chloro-6-{2-(2,4-di-t-amylphenoxy)butanamido}phenol In 40 ml of tetrahydrofuran and 60 ml of ethanol was dissolved 13 g ($20 \times 10^{-3}$ mole) of 2-nitro-3-pentafluoropropylamido-4-chloro-6-{2-(2,4-di-t-amylphenoxy)butanamido}phenol, and hydrogenation was effected by using 1.3 g of Pd-C as a catalyst. The color of the nitro derivative disappeared in 5 hours, and the Pd-C was removed by filtration and a solvent was evaporated therefrom under reduced pressure, followed by extraction of the residue with ethyl acetate. The ethyl acetate layer was washed with an aqueous sodium hydrogen carbonate solution and then with water, and after drying over magnesium sulfate, ethyl acetate was evaporated. Yield: 12.5 g.

Synthesis of 2,3-dipentafluoropropylamido-4-chloro-6-{2-(2,4-di-t-amylphenoxy)butanamido}phenol In 50 ml of ethyl acetate was dissolved 4 g ($6.4 \times 10^{-3}$ mole) of 2-amino-3-pentafluoropropylamido-4-chloro-6-{2-(2,4-di-t-amylphenoxy)butanamido}phenol, and 2.2 g of pentafluoropropionic acid anhydride was added to the solution and the mixture was refluxed under heating for 3 hours. After the reaction, a solvent was evaporated and the residue was separated and purified through column chromatography. Yield: 3.6 g (amorphous solid), FD-Mass: 768.

The cyan coupler of the present invention is used in a silver halide emulsion layer, primary in a red-sensitive emulsion layer, and its amount added may be in the range of $2 \times 10^{-3}$ to $8 \times 10^{-1}$ mole, preferably $1 \times 10^{-2}$ to $5 \times 10^{-1}$ mole, per one mole of silver halide.

As the method for incorporating the cyan coupler of the present invention in the silver halide emulsion layer, various methods may be employed. For example, it may be dissolved in a high boiling point organic solvent having a boiling point of 150° C. or higher such as alkyl phthalates (dibutyl phthalate, dioctyl phthalate, etc.), phosphates (diphenyl phosphate, triphenyl phosphate, tricresyl phosphate, dioctylbutyl phosphate), phenol derivatives (2,4-di-t-butylphenol, etc.), etc. and/or a low boiling point organic solvent having a boiling point of 30° to 150° C. (e.g., ethyl acetate, butyl acetate, ethyl propionate, sec-butyl alcohol, methyl isobutyl ketone, methyl cello-solve acetate, etc.) before dispersed in a hydrophilic colloid. Ordinarily, it is preferable to use a mixture of a high boiling point organic solvent and a low boiling point solvent.

The silver halide grains to be used in the silver halide emilsion layer of the light-sensitive silver haldie photographic material are not particularly limited, but silver iodobromide, silver bromide, silver halide, silver chlorobromide, silver chloroiodobromide or the like is preferred.

Crystals of these silver halide grains may be of regular crystals, twin crystals or others, and these can be used those having any ratio of {100} face to {111} face. Further, crystal structure of these silver halide grains may be uniform through inside to outside, or may be of layered structure comprising an inside and outside of different nature (a core-shell type). These silver halide grains may be also of the type such that a latent image is chiefly formed on the surface, or of the type wherein it is formed in the inside of a grain. Furthermore, platelike silver halide grains (see Japanese Provisional Patent Publications No. 113934/1983 and No. 47959/1986) can also be used.

The above silver halide grains may be substantially monodispersed or polydispersed.

As an emulsion for color negative, silver iodobromide is generally employed and a content of the silver iodobromide is preferably 10 mole % or less.

In light-sensitive materials for which particularly rapid developability is demanded such as printing papers for color, etc., they may be preferably silver chloride, silver chlorobromide or silver iodobromide containing silver chloride.

Particularly preferred as such silver halide grains are silver halide grains for rapid processing containing 90 mole % or more of silver chloride.

Such silver halide grains for rapid processing contain 90 mole % or more of silver chloride, with the silver bromide content being preferably 5 mole % or less and the silver iodide content being preferably 0.5 mole % or less. More preferably, silver chlorobromide with a silver bromide content of 0.1 to 1.0 mole % may be employed.

The silver halide grains for rapid processing may be used either alone or as a mixture with other silver halide grains having different compositions. Also, they can be used as a mixture with silver halide grains containing less than 10 mole % of silver chloride.

In the silver halide emulsion containing the silver halide grains for rapid processing, the proportion of the silver halide grains for rapid processing occupied in the total silver halide grains contained in these emulsion layers may be preferably 60% by weight or more, more preferably 80% by weight or more.

The silver halide to be used in the present invention may be also a polydisperse emulsion in which average grain sizes are distributed in wide range, but preferably a monodisperse emulsion.

The emulsion containing these silver halides may be chemically sensitized with an active gelatin, a sulfur sensitizer, a selenium sensitizer, a reductive sensitizer, a noble metal sensitizer, etc.

The silver halide to be used in the present invention may be optically sensitized with addition of an apropriate sensitizing dye in order to impart sensitivity to the respective desired light-sensitive wavelength regions.

The light-sensitive silver halide photographic material of the present invention comprising the above composition can be, for example, negative and positive films of color negative, and also a color printing paper.

The light-sensitive silver halide photographic material of the present invention, typically such color printing paper, is a light-sensitive silver halide photographic material for multi-color, and since color reproduction by the subtractive color photography is effected, it has ordinarily a structure having silver halide emulsion layers containing the respective couplers of magenta, yellow and cyan as the couplers for photography laminated in appropriate layer number and layer order on a support, but said layer number and layer order may be appropriately changed depending on the important performance, the purpose of use.

As a specific layer constitution of the light-sensitive silver halide photographic material to be used in the present invention, in case of a color printing paper, one having a yellow dye image forming layer, an intermediate layer, a magenta dye image forming layer, an intermediate layer, a cyan dye image forming layer, an intermediate layer and a protective layer arranged on a support successively from the support side is particularly preferred.

In the light-sensitive silver halide photographic material of the present invention, color fog preventives, image stabilizers, hardeners, plasticizers, polymer latices, UV-ray absorbers, formalin scavengers, mordants, development accelerators, development retarders, fluorescent brighteners, matting agents, lubricants, antistatic agents, surfactants, etc. can be used as desired.

For developing processing of the light-sensitive silver halide photographic material of the present invention, various color developing processings can be applied.

The light-sensitive silver halide photographic material of the present invention, by containing the cyan coupler of the present invention, has good sensitivity and color forming characteristic, and moreover, the cyan image formed became to have excellent fastness to light and heat.

EXAMPLES

The present invention is described in detail by referring to Examples, but the present invention is not limited thereto.

Example 1

On a paper support laminated on both surfaces with polyethylene, the respective layers shown below were successively provided by coating from the support side to prepare a silver halide color photographic material sample 1. The amounts of the compound added are shown per 1 $m^2$ (silver halide is calculated on silver) unless otherwise specifically noted.

Layer 1 ... a layer containing 1.2 g of gelatin, 0.32 g of blue-sensitive silver chlorobromide emulsion (containing 98 mole % of silver chloride) and 0.80 g of the yellow coupler (Y—1) shown below dissolved in 0.50 g of dioctyl phthalate.

Layer 2 ... an intermediate layer comprising 0.70 g of gelatin, 8 mg of the irradiation dyes (AI—1) shown below and 4 mg of (AI—2) shown below.

Layer 3 ... a layer containing 1.25 g of gelatin, 0.20 g of a green-sensitive silver chlorobromide emulsion (containing 99 mole % of silver chloride) and 0.62 g of the magenta coupler (M—1) dissolved in 0.30 g of dioctyl phthalate.

Layer 4 ... an intermediate layer comprising 1.20 g of gelatin.

Layer 5 ... a layer containing 1.20 g of gelatin, 0.30 g of a red-sensitive silver chlorobromide emulsion (containing 99 mole % of silver chloride) and 0.45 g of the cyan coupler (C—1) dissolved in 0.20 g of dioctyl phthalate.

Layer 6 ... a layer containing 1.00 g of gelatin and 0.30 g of the UV-ray absorber (UV—1) dissolved in 0.20 g of dioctyl phthalate.

Layer 7 ... a layer containing 0.50 g of gelatin.

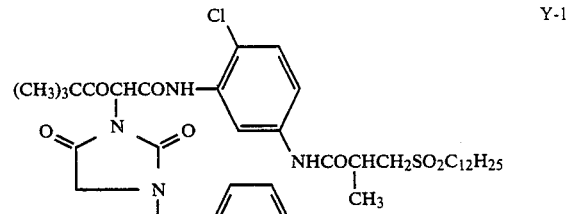

Y-1

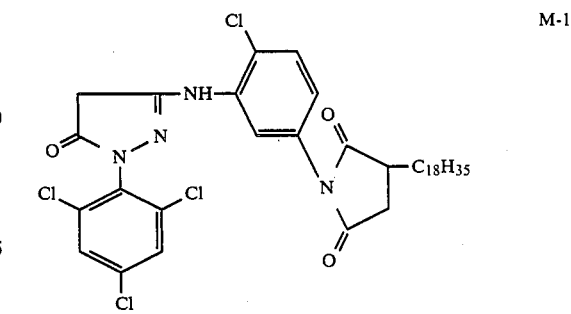

M-1

-continued

[Structure C-1: dichloro-methyl-hydroxyphenyl NHCOCH(C2H5)O- pentylphenyl with C5H11(t)]

[Structure AI-1: anthraquinone sulfonate dye]

[Structure AI-2: bis-pyrazolone pentamethine dye with HOOC, SO3K, KO3S groups]

[Structure UV-1: benzotriazole with hydroxyphenyl and two C5H11(t) groups]

As the hardener, 2,4-dichloro-6-hydroxy-s-triazine sodium was added in the layers 2, 4 and 7, each to an amount of 0.017 g per 1 g of gelatin.

Also, samples 2 to 5 were prepared in the same manner as the above sample 1, except for replacing the cyan coupler (C—1) in the layer 5 in the above sample 1 with the Control couplers and the couplers of the present invention as shown in Table 1. The cyan couplers were added each in the amount equimolar to the cyan coupler (C—1).

Each of the above light-sensitive samples 1 to 5 was exposed to light through an optical wedge and then processed according to the following steps.

Processing steps

| | | |
|---|---|---|
| Color developing | 35° C. | 45 sec. |
| Bleach-fixing | 35° C. | 45 sec. |
| Stabilizing | 35° C. | 1 min. 30 sec. |
| Drying | 60 to 80° C. | 2 min. |

The respective processing solutions had the following compositions.

| [Color developing solution] | |
|---|---|
| Water | 800 ml |
| Triethanol amine | 11 ml |
| N,N—diethylhydroxylamine (85% aqueous solution) | 6 ml |
| Potassium chloride | 2.3 g |
| Potassium sulfite | 0.3 g |
| Potassium carbonate | 30 g |
| Sodium tetrapolyphosphate | 2.0 g |
| N—ethyl-N—β-methanesulfonamidoethyl-3-ethyl-4-aminoaniline sulfate | 5.2 g |

Made up to one liter with addition of water, and adjusted to pH=10.1 with a 20% potassium hydroxide or a 10% diluted sulfuric acid.

| [Bleach-fixing solution] | |
|---|---|
| Water | 800 ml |
| Iron (III) ammonium ethylenediaminetetraacetate | 65 g |
| 2-Sodium ethylenediaminetetraacetate | 5 g |
| Ammonium thiosulfate | 60 g |
| Sodium hydrogen sulfite | 10 g |
| Sodium metabisulfite | 2 g |
| Sodium chloride | 10 g |

Made up to one liter with addition of water, and adjusted to pH=5.6 with diluted sulfuric acid.

| [Stabilizing solution] | |
|---|---|
| 5-Chloro-2-methyl-4-isothiazolin-3-one | 1.0 g |
| 1-Hydroxyethylidene-1,1-diphosphonic acid | 2.0 g |

Made up to one liter with addition of water, and adjusted to pH=7.0 with sulfuric acid or potassium hydroxide.

Each sample after the above processing was subjected to sensitometry to determine the maximum density ($D_{max}$) and the sensitivity of the red-sensitive emulsion layer.

Also, the above processed sample was irradiated by xenon fadometer for 5 days for examination of light resistance of the cyan image.

The storage stability (dark fading characteristic) of the cyan image was also examined by storing the above processed sample under high temperature and high humidity of 80° C., 90% RH (relative humidity) for 2 weeks. The results are shown in Table 1.

TABLE 1

| Sample No. | Coupler | *1 Sensitivity | Maximum density | *2 Light resistance | *3 Image storability |
|---|---|---|---|---|---|
| 1 (Control) | C-1 | 100 | 2.28 | 0.89 | 0.81 |
| 2 (Control) | C-2 | 85 | 1.78 | 0.85 | 0.96 |
| 3 (This invention) | I-1 | 102 | 2.31 | 0.90 | 0.96 |
| 4 (This invention) | I-2 | 104 | 2.35 | 0.88 | 0.97 |
| 5 (This invention) | I-6 | 101 | 2.32 | 0.91 | 0.98 |

*1 relative value to sensitivity of sample 1 as 100.
*2 density afer deterioration of the portion with initial density of 1.0.
*3 density after deterioration of the portion with initial density of 1.0.

[Structure C-2: hydroxyphenyl with C5H11(t), (t)C5H11, OCH(C3H7(i))CONH, Cl, NHCO-pentafluorophenyl]

As is apparent from the results shown in Table 1, the sample 1 by use of the Control coupler C—1 is insufficient in image storage stability (dark fading characteristic), while the sample 2 by use of the Control coupler C—2 is insufficient in sensitivity and color forming characteristic (maximum density).

In contrast, the samples 3, 4 and 5 by use of the cyan couplers of the present invention have good sensitivity and color forming characteristic (maximum density), and yet also excellent in light resistance, image storability (dark fading characteristic).

Example 2

The coupler C—3 shown below (10 g), 10 g of dioctyl phthalate and 20 ml of ethyl acetate were completely dissolved by heating to 50° C., and the resultant solution was mixed and stirred with 10 g of gelatin and 100 ml of an aqueous solution containing 0.4 g of Alkanol XC (sodium diisopropylnaphthalene sulfonate, produced by Du Pont), and then finely emulsified by sonication. The coupler dispersion was added into 400 g of a photographic emulsion containing 35 g of silver chlorobromide (containing 99% of silver chloride) and 40 g of gelatin and, after addition of 40 ml of a 2% aqueous solution of 2,4-dichloro-6-hydroxy-s-triazine sodium as the hardener, with adjustment of the pH to 6.0, the mixture was uniformly applied on a triacetylcellulose film base subjected to subbing to provide a sample 6.

Next, samples 7, 8 and 9 were prepared similarly as sample 6, except for using equal moles of the cyan coupler I—4, 5 or 8 of the present invention in place of the coupler C—3.

These samples were exposed by use of a wedge for sensitometry, and then subjeccted to the same color developing, bleach-fixing and stabilizing processing as in Example 1, followed by determination of sensitivity and maximum density.

The respective processed samples were also irradiated by a xenon fadometer for 5 days for examination of light stability of the cyan image. The results obtained are shown in Table 2.

TABLE 2

| Sample No. | Coupler | *4 Sensitivity | Maximum density | *5 Light stability |
|---|---|---|---|---|
| 6 (Control) | C-3 | 100 | 1.25 | 0.48 |
| 7 (This invention) | I-4 | 103 | 1.28 | 0.77 |
| 8 (This invention) | I-5 | 101 | 1.30 | 0.75 |
| 9 (This invention) | I-8 | 104 | 1.32 | 0.78 |

*4 relative value to sensitivity of sample 6 as 100.
*5 density after deterioration of the portion with initial density of 1.0.

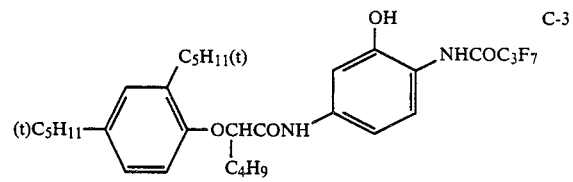

C-3

As is apparent from the results shown in Table 2, also in this Example in which a tetra-equivalent cyan coupler is employed, the light-sensitive silver halide photographic material exhibits excellent effects.

Also, the present invention exhibits good effects in a light-sensitive silver halide photographic material constituted of a single layer similarly as in the case of a light-sensitive silver halide photographic material constituted of multiple layers.

Example 3

(Preparation of silver halide emulsion)

Six kinds of silver halide emulsions as shown in Table 3 were prepared according to the neutral method or simultaneous mixing method.

TABLE 3

| Emulsion No. | AgCl % | AgBr % | Average grain diameter (μm) | Chemical sensitizer | Spectral sensitizing dye |
|---|---|---|---|---|---|
| Em-1 | 99.5 | 0.5 | 0.67 | Sodium | SD-1*3 |
| Em-2 | 99.5 | 0.5 | 0.46 | thiosulfate*1 | SD-2*4 |
| Em-3 | 99.5 | 0.5 | 0.43 | Chloroplatinic acid*2 | SD-3*5 |
| Em-4 | 10 | 90 | 0.67 | Sodium | SD-1*3 |
| Em-5 | 30 | 70 | 0.46 | thiosulfate*1 | SD-2*4 |
| Em-6 | 30 | 70 | 0.43 |  | SD-3*5 |

*1 added 2 mg per one mole of silver halide
*2 added $5 \times 10^{-5}$ mole per one mole of silver halide
*3 added $0.9 \times 10^{-3}$ mole per one mole of silver halide
*4 added $0.7 \times 10^{-3}$ mole per one mole of silver halide
*5 added $0.2 \times 10^{-3}$ mole per one mole of silver halide Each silver halide emulsion was added STB—1 as shown below as an emulsion stabilizer with an amount of $5 \times 10^{-3}$ mole per one mole of silver halide after completion of the chemical sensitization.

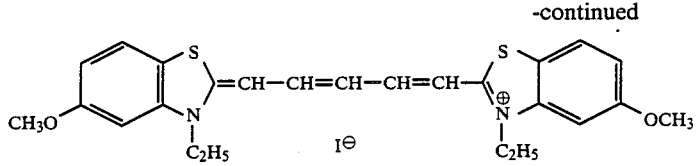
SD-3

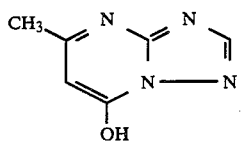
STB-1

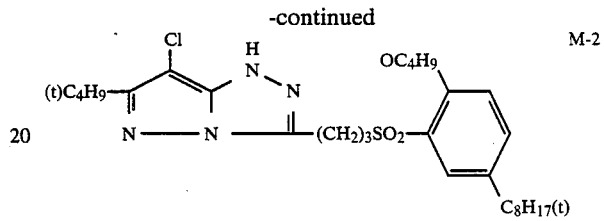
M-2

(Preparation of sample of silver halide color photographic material)

Then, the following layers 1 to 7 were successively coated (simultaneous coating) on a paper support coated both surfaces thereof with a polyethylene to prepare silver halide color photographic materials 10 to 15 (in the following, added amounts are all shown by an amount per 1 m² of the light-sensitive material.).

Layer 1 ... a layer containing gelatin (1.2 g), 0.29 g (in terms of silver, hereinafter the same) of a blue-sensitive silver halide emulsion (Em—1) and 0.3 g of dinonylphthalate (DNP) dissolved 0.75 g of yellow coupler (Y—1), 0.3 g of light stabilizer ST—1 and 0.015 g of 2,5-dioctylhydroquinone (HQ—1) therein.

Layer 2 ... a layer containing gelatin (0.9 g), and 0.2 g of dioctylphthalate (DOP) dissolved 0.04 g of HQ—1 therein.

Layer 3 ... a layer containing gelatin (1.4 g), 0.2 g of a green-sensitive silver halide emulsion (Em—2), 0.50 g of magenta coupler (M—2), 0.25 g of light stabilizer (ST-2), 0.3 g of DOP dissolved 0.01 g of HQ—1, and 6 mg of the filter dye (AI—2).

Layer 4 ... a layer containing gelatin (1.2 g) and 0.3 g of DNP dissolved 0.6 g of the ultraviolet-ray absorber (UV—1) and 0.05 g of HQ—1 therein.

Layer 5 ... a layer containing gelatin (1.4 g), 0.20 g of a red-sensitive silver halide emulsion (Em—3) and 0.3 g of DOP dissolved 0.9 mmole of the cyan coupler as shown in Table 4 and 0.01 g of HQ—1 therein.

Layer 6 ... a layer containing gelatin (1.1 g), 0.2 g of DOP dissolved 0.2 g of UV—1 therein, and 5 mg of the filter dye (AI—1).

Layer 7 ... a layer containing gelatin (1.0 g) and 0.05 g of sodium 2,4-dichloro-6-hydroxytriazine.

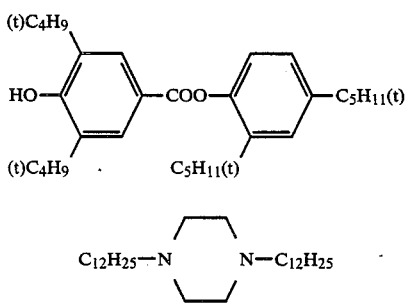
ST-1

ST-2

After processings were carried out according to the color developing processing steps, sensitivity of the red-sensitive emulsion layer (inverse number of exposed amount providing a density of fog+0.1) and the maximum density ($D_{max}$) by using a photodensitometer (available from KONICA CORPORATION).

Also, the resulting samples were preserved at 85° C. and 60% relative humidity for 25 days, and by measuring a density after deterioration of the dye image at an initial density of 1.0, dark color fading property was evaluated. The results are shown in Table 4.

| [Processing steps] | Temperature | Time |
| --- | --- | --- |
| Color developing | 34.7 ± 0.3° C. | 45 sec. |
| Bleach-fixing | 34.7 ± 0.5° C. | 50 sec. |
| Stabilizing | 30 to 34° C. | 90 sec. |
| Drying | 60 to 80° C. | 60 sec. |

The respective processing solutions had the following compositions.

| [Color developing solution] | |
| --- | --- |
| Water | 800 ml |
| Triethanol amine | 8 g |
| N,N—diethylhydroxylamine | 5 g |
| Potassium chloride | 2 g |
| N—ethyl-N—β-methanesulfonamidoethyl-3-ethyl-4-aminoaniline sulfate | 5 g |
| Sodium tetrapolyphosphate | 2 g |
| Potassium carbonate | 30 g |
| Potassium sulfite | 0.2 g |
| Fluorescent brightener (4,4'-diaminostylbene-disulfonic acid derivative) | 1 g |

Made up to one liter with addition of water, and adjusted to pH 10.2.

| [Bleach-fixing solution] | |
| --- | --- |
| Ferric ammonium ethylenediaminetetraacetate dihydrate | 60 g |
| Ethylenediaminetetraacetic acid | 3 g |
| Ammonium thiosulfate (70% aqueous solution) | 100 ml |
| Ammonium sulfite (40% aqueous solution) | 27.5 ml |

Made up to one liter with addition of water, and adjusted to pH 5.7 with glacial acetic acid.

| [Stabilizing solution] | |
| --- | --- |
| 5-Chloro-2-methyl-4-isothiazolin-3-one | 1 g |
| 1-Hydroxyethylidene-1,1-diphosphonic acid | 2 g |

Made up to one liter with addition of water, and adjusted to pH 7.0 with sulfuric acid or potassium hydroxide.

On the other hand, 5 g of sodium hydrosulfite was added to the bleach-fixing solution to decrease bleaching power and it was used as a fatigue bleach-fixing solution (hereinafter referred to as "fatigue BF") to examine color reproducibility.

That is, after color developing processing, two kinds of bleach-fixing processings using a new solution of the bleach-fixing solution (hereinafter referred to as "new BF") and a fatigue bleach-fixing solution were applied, and by comparing the maximum density of the resulting cyan dye, color reproducibility (%) was calculated due to the following equation.

$$\text{Color reproducibility (\%)} = \frac{\text{Maximum density in case of fatigue } BF}{\text{Maximum density in case of new } BF} \times 100$$

Comparative coupler C-4

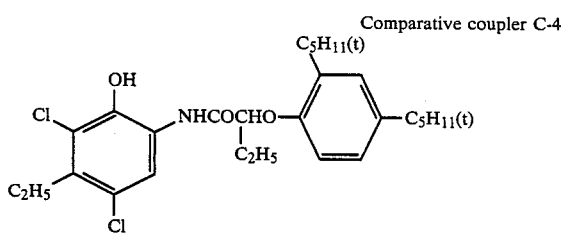

TABLE 4

| Sample No. | Coupler | Sensitivity* | $D_{max}$ | Image storability | Color reproducibility (%) |
| --- | --- | --- | --- | --- | --- |
| 10 (Control) | C - 1 | 100 | 2.56 | 0.71 | 65 |
| 11 (Control) | C - 4 | 98 | 2.52 | 0.83 | 70 |
| 12 (This invention) | II - 4 | 105 | 2.62 | 0.91 | 93 |
| 13 (This invention) | II - 5 | 102 | 2.63 | 0.90 | 92 |
| 14 (This invention) | II - 7 | 103 | 2.59 | 0.89 | 90 |
| 15 (This invention) | II - 9 | 100 | 2.57 | 0.88 | 91 |

*sensitivity is shown by a relative value when sensitivity of sample 10 as 100.

As seen from Table 4, it can be understood that when the cyan coupler of the present invention is used, high maximum density and sensitivity can be obtained and heat resistivity of the obtained cyan image is good.

Further, with respect to color reproducibility which is an important point for rapid processing, it can be also understood that the coupler of the present invention is positioned at extremely higher level as compared with the conventional couplers.

Also, with respect to these samples 10 to 15, color reproducibility of these samples when printings were effected under the conditions of which color negative and neutral were combined and photographying a color checker (produced by Macbeth Co.) with Konica color GX-100 was evaluated with eyes.

As compared with the sample No. 10, each of Samples 12 to 15 of the present invention is extremely improved in discrimination of blue and cyan as well as color reproducibility of green color and red to magenta.

From the facts as mentioned above, it can be understood that the compound represented by the formula (II) is a cyan coupler particularly suitable for a color paper.

Example 4

Samples No. 16 to 21 of light-sensitive silver halide color photographic materials were prepared in the same manner as in Example 3 except that the blue-sensitive silver halide emulsion in layer 1 of the light-sensitive silver halide color photographic material prepared in Example 3 was replaced by Em—4 in Table 3, the green-sensitive silver halide emulsion in layer 3 by Em—5 of the same, and the red-sensitive silver halide emulsion in layer 5 by Em—6, respectively.

The samples obtained were subjected to wedge-exposure with use of the photosensitometer KS—7 type (produced by KONICA CORPORATION), followed by processing with the following color developing processing step and measurements were carried out in the same manner as in Example 3.

The results are shown in Table 5.

| [Processing steps] | | |
| --- | --- | --- |
| Color developing | 3 min 30 sec | temperature 33° C. |
| Bleach-fixing | 1 min 30 sec | temperature 33° C. |
| Washing | 3 min | temperature 33° C. |

Color developing solution prescription

| | |
| --- | --- |
| N—ethyl-N—β-methanesulfonamidoethyl-3-methyl-4-aminoaniline sulfate | 4.9 g |
| Hydroxylamine sulfate | 2.0 g |
| Potassium carbonate | 25.0 g |
| Potassium bromide | 0.6 g |
| Anhydrous sodium sulfite | 2.0 g |
| Benzyl alcohol | 13 ml |
| Polyethylene glycol (average polymerization degree: 400) | 3.0 ml |

Made up to one liter with addition of water, and adjusted to pH 10.0 with sodium hydroxide.

Bleach-fixing solution prescription

| | |
| --- | --- |
| Iron sodium ethylenediaminetetraacetate | 6.0 g |
| Ammonium thiosulfate | 100 g |
| Sodium bisulfite | 10 g |
| Sodium metabisulfite | 3 g |

Made up to one liter with addition of water, and adjusted to pH 7.0 with aqueous ammonia.

TABLE 5

| Sample No. | Coupler | Sensitivity* | $D_{max}$ | Image storability |
| --- | --- | --- | --- | --- |
| 16 (Control) | C - 1 | 100 | 2.58 | 0.75 |
| 17 (Control) | C - 4 | 100 | 2.60 | 0.91 |
| 18 (This invention) | II - 4 | 115 | 2.71 | 0.96 |
| 19 (This invention) | II - 5 | 110 | 2.62 | 0.93 |
| 20 (This invention) | II - 7 | 113 | 2.63 | 0.93 |

TABLE 5-continued

| Sample No. | Coupler | Sensitivity* | $D_{max}$ | Image storability |
|---|---|---|---|---|
| 21 (This invention) | II-9 | 105 | 2.65 | 0.94 |

* sensitivity is shown in the same manner as in Example 3 by a relative value when sensitivity of sample 16 as 100.

As described above, substantially the same results can be obtained as in Example 3.

Example 5

The following emulsions were prepared.

Preparation of emulsion S

To 750 ml of 2.0% inactive gelatin solution maintained at 50° C. were added the following A1 and B solutions simultaneously while stirring and injected over 3 minutes. After ripenning for 25 minutes, excessive salts were removed by the precipitation washing method and then redispersed and the following C1 and D1 solutions were added. After 10 minutes, excessive water-soluble salts were again removed and silver halide grains were dispersed by adding a small amount of gelatin.

Preparation of emulsion L

To 750 ml of 1.5% inactive gelatin solution maintained at 60° C. were added the following A2 and B solutions simultaneously while stirring and injected over 15 minutes. After ripenning for 40 minutes, excessive salts were removed by the precipitation washing method and then redispersed and 10 mg of hypo was added thereto, and the following C2 and D2 solutions were added. After 10 minutes, excessive water-soluble salts were again removed and silver halide grains were dispersed by adding a small amount of gelatin.

Preparation of emulsion M

To 750 ml of 2.0% inactive gelatin solution maintained at 50° C. were added the following A3 and B solutions simultaneously while stirring and injected over 5 minutes. After ripenning for 25 minutes, excessive salts were removed by the precipitation washing method and then redispersed and the following C1 and D2 solutions were added. After 10 minutes, excessive water-soluble salts were again removed and silver halide grains were dispersed by adding a small amount of gelatin.

| | | | |
|---|---|---|---|
| A1 solution | Water | 2000 ml | |
| | NaCl | 35 g | |
| | NH4Br | 109.6 g | |
| | KI | 0.8 g | |
| A2 solution | Water | 1000 ml | |
| | NaCl | 26.3 g | |
| | NH4Br | 109.6 g | |
| | KI | 0.8 g | |
| A3 solution | Water | 1000 ml | |
| | NaCl | 33.8 g | |
| | KBr | 12 g | |
| B solution | Water | 1200 ml | |
| | AgNO3 | 170 g | |
| C1 solution | Water | 1000 ml | |
| | NaCl | 60 g | |
| | NH4Br | 6.9 g | |
| C2 solution | Water | 1000 ml | |
| | NaCl | 31.6 g | |
| D1 solution | Water | 1000 ml | |
| | AgNO3 | 70 g | |
| | Water | 1000 ml | |
| D2 solution | AgNO3 | 80 g | |

To the three kinds of emulsions, the following sensitizing dyes, couplers, etc. are added and they are coated on a support to form a multi-layer light-sensitive color material.

Red-sensitive emulsion layer (first layer)

To the emulsion S and the emulsion M was added a coupler solution which is protect dispersed containing sensitizing dyes (SD—6) and (SD—7), stabilizers (STB—1) and (STB—2), a surfactant (S—2), and further added dibutyl phthalate, ethyl acetate, a surfactant (S—2), 2,5-dioctylhydroquinone and cyan couplers (C—1) and (C—2), respectively.

Gelatin was added to the mixture and each of emulsions was mixed to coat so as to become the gamma value being 1.5.

First intermediate layer (second layer)

A gelatin solution containing a protect dispersed solution containing dioctyl phthalate, 2,5-dioctylhydroquinone, a UV absorber Tinuvin 328 (trade name, produced by Chiba Geigy AG) and surfactant (S—1) was prepared and coated so as to become a Tinuvin coated amount being 0.15 g/m².

Green-sensitive emulsion layer (third layer)

To the emulsion S and the emulsion M was added a coupler solution which is protect dispersed containing a sensitizing dye (SD—5), stabilizers (STB—1) and (STB—2), a surfactant (S—2), and further dibutyl phthalate, ethyl acetate, 2,5-dioctylhydroquinone, a surfactant (S—1) and a magenta coupler (M—3).

Gelatin was added and a hardener (H—1) was further added and coated so as to become the gamma value of the resulting emulsion being 1.5.

Second intermediate layer (fourth layer)

The same prescription as in the first intermediate layer and coated so as to become a Tinuvin 328 coated amount being 0.2 g/m².

Yellow filter layer (fifth layer)

By adding a yellow colloidal silver prepared by oxidizing in the presence of an alkaline weak reducing agent (the weak reducing agent was removed by the nudel washing method after neutralization) as well as dioctyl phthalate, ethyl acetate, a surfactant (S—1), 2,5-dioctylhydroquinone solution, a surfactant (S—2) and a hardener (H-1), it was coated so as to become a colloidal silver coated amount being 0.15 g/m².

Third intermediate layer (sixth layer)

The same as in the first intermediate layer.

Blue-sensitive emulsion layer (seventh layer)

To the emulsion L, the emulsion S and the emulsion M was added a coupler solution which is protect dispersed containing a sensitizing dye (SD—4), stabilizers (STB—1) and (STB—3), a surfactant (S—2), and further dibutyl phthalate, ethyl acetate, 2,5-dioctylhydroquinone, a surfactant (S—1) and a yellow coupler (Y—2).

Gelatin was added and a hardener (H—1) was further added and coated so as to become the gamma value of the resulting emulsion being 1.5.

Fourth intermediate layer (eighth layer)

The same prescription as in the first intermediate layer and coated so as to become a Tinuvin 328 coated amount being 0.35 g/m².

Protective layer (ninth layer)

By using a gelatin solution containing a colloidal silica, a surfactant (S—2), hardeners (H—2) and (H—3), and coated so as to become a gelatin coated amount being 1.0 g/m².

On a polyethylene laminated paper which was surface treated were coated the first layer to the ninth layer according to the simultaneous coating method and then dried (Sample 22).

Further, in the same manner as in the above except that the cyan coupler in the red-sensitive emulsion layer (first layer) was replaced as shown in Table 6 by an equimolar amount of a coupler of the present invention, samples No. 23 to No. 27 were prepared.

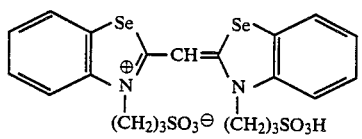

SD-4

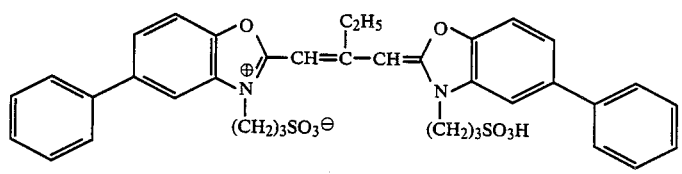

SD-5

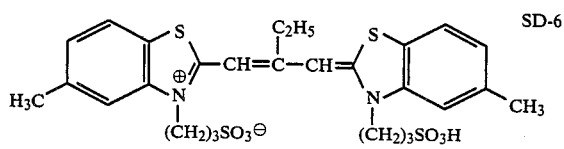

SD-6

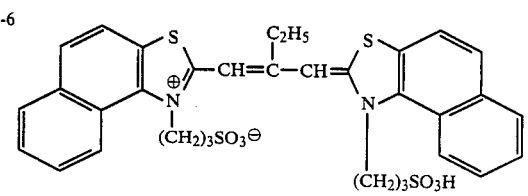

SD-7

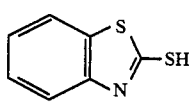

STB-2

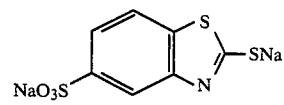

STB-3

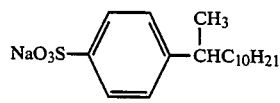

S-1

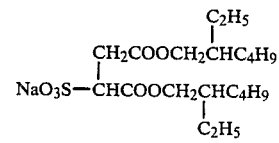

S-2

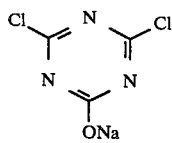

H-1

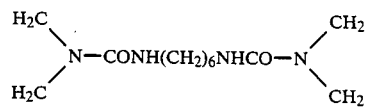

H-2

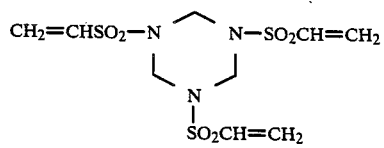

H-3

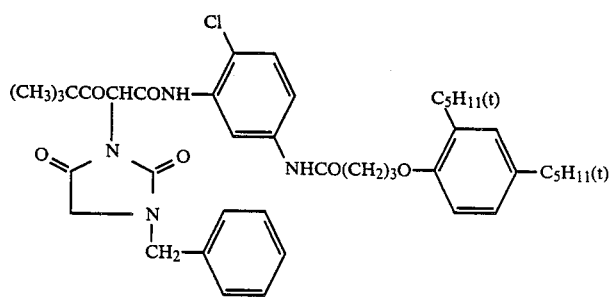

Y-2

-continued

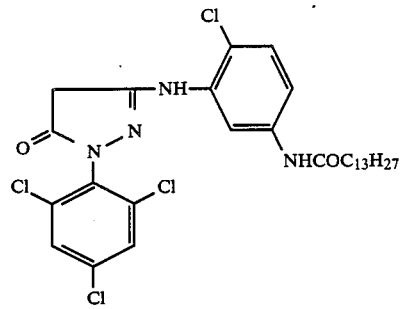

M-3

To the light-sensitive materials prepared by the above procedures, white wedge exposure was effected and then the developing processing was effected following the steps as shown below to obtain a neutral positive wedge.

A density of a cyan image at a density of 1.0 after preservation at 85° C., under 60% relative humidity for 20 days was measured as well as $D_{max}$ of a cyan image thereof was measured. The results are shown in Table 6.

In the table, an emulsion composition in the respective light-sensitive layer shows parts by weight.

Processing steps (processing temperature and processing time)

| | | |
|---|---|---|
| [1] Impregnation (in color developing solution) | 38° C. | 8 sec |
| [2] Fog exposure | — | 10 sec at 1 lux |
| [3] Color developing | 38° C. | 2 min |
| [4] Bleach-fixing | 35° C. | 60 sec |
| [5] Stabilizing processing | 25 to 30° C. | 1 min 30 sec |
| [6] Drying | 75 to 80° C. | 1 min |

Composition of processing solutions
(Color developing solution)

| | |
|---|---|
| Benzyl alcohol | 10 ml |
| Ethylene glycol | 15 ml |
| Potassium sulfite | 2.0 g |
| Potassium bromide | 1.5 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-Methyl-4-amino-N—ethyl-N—(β-methane-sulfonamidoethyl)aniline sulfate | 5.5 g |
| Fluorescent brightener (4,4'-diamino-styrbenedisulfonic acid derivative) | 1.0 g |
| Potassium hydroxide | 2.0 g |

Made up to one liter with addition of water and adjusted to pH 10.20.

(Bleach-fixing solution)

| | |
|---|---|
| Ferric ammonium ethylenediaminetetraacetate dihydrate | 60 g |
| Ethylenediaminepentaacetic acid | 3 g |
| Ammonium thiosulfate (70% solution) | 100 ml |
| Ammonium sulfite (40% solution) | 27.5 ml |

Made up to one liter with addition of water and adjusted to pH 7.1 with potassium carbonate or glacial acetic acid.

(Stabilizing solution)

| | |
|---|---|
| 5-Chloro-2-methyl-4-isothiazolin-3-one | 1.0 g |
| Ethylene glycol | 10 g |
| 1-Hydroxyethyliden-1,1'-diphosphonic acid | 2.5 g |
| Bismuth chloride | 0.2 g |
| Magnesium chloride | 0.1 g |
| Ammonium hydroxide (28% aqueous solution) | 2.0 g |
| Sodium nitrilotriacetate | 1.0 g |

Made up to one liter with addition of water and adjusted to pH 7.0 with ammonium hydroxide or sulfuric acid.

Provided that the stabilizing processing is made a counter-current system of two tanks constitution.

TABLE 6

| Sample No. | Coupler | $D_{max}$ | Image storability |
|---|---|---|---|
| 22 (control) | C - 1<br>C - 2 | 2.19 | 0.87 |
| 23 (This invention) | II - 4 | 2.30 | 0.93 |
| 24 (This invention) | II - 5 | 2.31 | 0.92 |
| 25 (This invention) | IV - 4 | 2.45 | 0.95 |
| 26 (This invention) | IV - 5 | 2.48 | 0.97 |
| 27 (This invention) | IV - 6 | 2.50 | 0.96 |

As described above, it can be understood that the couplers represented by the formulae (II) and (IV) of the present invention are suitable for a direct positive emulsion since they are excellent in coloring property and also good in heat resistance. Also, by setting the light-sensitive material in KONICA Color 7 (trade name) and scanning exposure was carried out with a constant rate of 5 cm/sec from a rectangular slit having 1×20 cm to effect copying a color checker (produced by Macbeth Co.). As results, with respect to samples No. 23 to 27, hue difference of cyan and blue can be clearly understood as compared with control salme No. 22 whereby color reproduction of red to magenta has improved.

Example 6

On a triacetylcellulose film support which had been carried out a subbing treatment with a copolymer of maleic acid anhydride and vinyl acetate after carried out antistatic treatment to a back surface, each layer having the following composition was coated successively from the support side to form a multi-layer light-sensitive color material sample No. 28. An amount added shows per one mole of silver halide otherwise described particularly.

<Back surface antistatic treatment>

| | | |
|---|---|---|
| Back surface first layer: | Stearic acid | 20 mg/m² |
| | Diacetylcellulose | 10 mg/m² |
| | Alumina sol | 1 g/m² |
| Back surface second layer: | Diacetylcellulose | 50 mg/m² |
| | Stearic acid | 10 mg/m² |
| | Silica matting agent (average grain diameter: 3 μm) | 50 mg/m² |

<On the support>

First layer: an antihalation layer
  0.3 g/m² of a ultraviolet-ray absorber UV—2, 0.4 g/m² of a ultraviolet-ray absorber UV—3, 0.24 g/m² of black colloidal silver and 2.7 g/m² of gelatin.

Second layer: an intermediate layer
  0.1 g/m² of 2,5-di-t-octylhydroquinone and 1.0 g/m² of gelatin.

Third layer: Low-sensitivity red-sensitive silver halide emulsion layer
  Monodispersed emulsion (emulsion I) comprising AgBrI containing 2.5 mole % of AgI having an average grain diameter of 0.35 μm . . . silver amount: 0.5 g/m², SD—8 . . . $7.6 \times 10^{-4}$ mole,
  Coupler C—3 . . . 0.1 mole and 0.9 g/m² of gelatin.

Fourth layer: High-sensitivity red-sensitive silver halide emulsion layer
  Monodispersed emulsion (emulsion II) comprising AgBrI containing 2.5 mole % of AgI having an average grain diameter of 0.75 μm . . . silver amount: 0.8 g/m², SD—8 . . . $3.2 \times 10^{-4}$ mole,
  Coupler C—3 . . . 0.2 mole and 1.75 g/m² of gelatin.

Fifth layer: Intermediate layer
  0.1 g/m² of 2,5-di-t-octylhydroquinone and 0.9 g/m² of gelatin.

Sixth layer: Low-sensitivity green-sensitive silver halide emulsion layer
  Emusion I . . . silver amount: 1.0 g/m²,
  SD—9 . . . $6.6 \times 10^{-4}$ mole,
  SD—10 . . . $0.6 \times 10^{-4}$ mole,
  Coupler M—4 . . . 0.05 mole and 0.8 g/m² of gelatin.

Seventh layer: High-sensitivity green-sensitive silver halide emulsion layer
  Emulsion II . . . silver amount: 1.0 g/m²,
  SD—9 . . . $2.76 \times 10^{-4}$ mole,
  SD—10 . . . $0.23 \times 10^{-4}$ mole,
  Coupler M—4 . . . 0.15 mole and 1.5 g/m² of gelatin.

Eighth layer: Intermediate layer
  The same as in the fifth layer.

Ninth layer: Yellow filter layer
  0.1 g/m² of yellow colloidal silverr, 0.9 g/m² of gelatin and 0.1 g/m² of 2,5-di-t-octylhydroquinone.

Tenth layer: Low-sensitivity blue-sensitive silver halide emulsion layer
  Monodispersed emulsion (emulsion III) comprising AgBrI containing 2.5 mole % of AgI having an average grain diameter of 0.6 μm . . . silver amount: 0.4 g/m²,
  SD—11 . . . $2.65 \times 10^{-4}$ mole,
  Coupler Y—3 . . . 0.3 mole and 1.3 g/m² of gelatin.

Eleventh layer: High-sensitivity blue-sensitive silver halide emulsion layer
  Monodispersed emulsion (emulsion IV) comprising AgBrI containing 2.5 mole % of AgI having an average grain diameter of 1.0 μm . . . silver amount: 0.8 g/m²,
  SD—11 . . . $1.59 \times 10^{-4}$ mole,
  Coupler Y—3 . . . 0.3 mole and 2.1 g/m² of gelatin.

Twelfth layer: First protective layer
  0.3 g/m² of UV—2, 0.4 g/m² of UV—3, 1.2 g/m² of gelatin and 0.1 g/m² of 2,5-di-t-octylhydroquinone.

Thirteenth layer: Second protective layer
  Non-light-sensitive fine particle silver halide emulsion comprising AgBrI containing 1 mole % of AgI having an average grain diameter of 0.06 μm . . . silver amount: 0.3 g/m², a polyethylmethacrylate particle (diameter: 1.5 μm), 0.7 g/m² of gelatin and a surfactant S—3.

In the respective layer, in addition to the above composition, H—1 or a surfactant was added thereto. Also, as a solvent for a coupler, tricresylphosphate was employed.

All the emulsions used are monodisperse octahedral emulsions and are those prepared by the double jet method in which seed grains having 0.095 μm or 0.25 μm (average silver iodide content of 2 mole %) are grown at 45° C. in the presence of ammonia while controlling pAg and pH. Silver iodide contents in a core, an intermediate layer and a shell were varied by changing a composition of silver halide to be added.

For growth of a core/sheel type silver halide emulsion, the methods as disclosed in Japanese Provisional Patent Publications No. 52238/1984, No. 138538/1985, No. 49938/-1983 and No. 122935/1985 have been used.

(Compounds used for preparing samples)
Ultraviolet-ray absorber UV—2

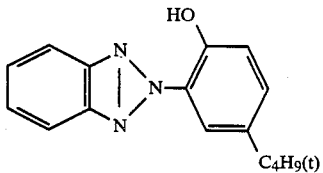

Ultraviolet-ray absorber UV—3

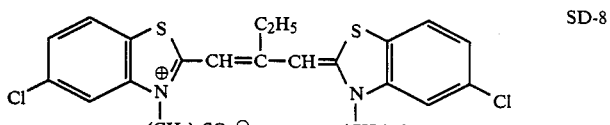

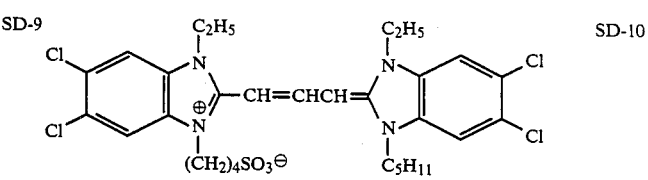

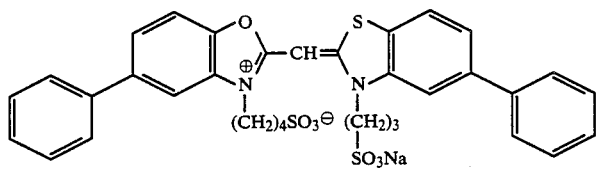

SD-11

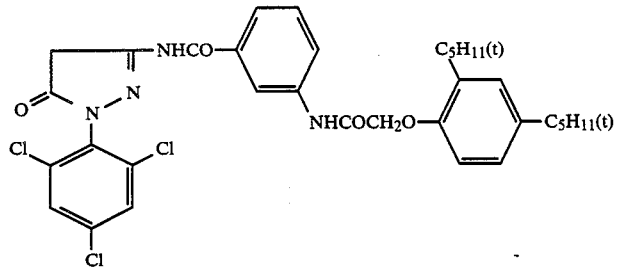

M-4

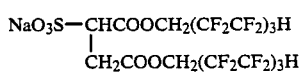

S-3

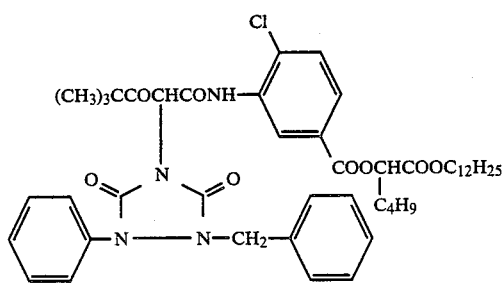

Y-3

Next, by replacing the cyan coupler C—3 in the third layer and the fourth layer of the sample No. 28 with couplers of the present invention as shown in Table 7, samples No. 29 to No. 33 were prepared.

After samples No. 28 to No. 33 were subjected to wedge exposure and then the following reversal process was subjected to, $D_{max}$ of the cyan image was measured by a red light. Also, color checker (produced by Macbeth Co.) was photographed by actually using the samples No. 28 to No. 33, and after subjected to reverse treatment, color reproducibility was evaluated with eyes.

The results are shown in Table 7.

| Processing steps | Processing time | Processing temperature |
|---|---|---|
| First developing | 6 min | 38° C. (±0.3) |
| Washing | 2 min | 38° C. (±0.3) |
| Reversing | 2 min | 38° C. (±0.3) |
| Color developing | 6 min | 38° C. (±0.3) |
| Adjustment | 2 min | 38° C. (±0.3) |
| Bleaching | 6 min | 38° C. (±0.3) |
| Fixing | 4 min | 38° C. (±0.3) |
| Washing | 4 min | 38° C. (±0.3) |
| Stabilizing | 1 min | normal temperature |
| Drying | | |

| First developing solution | |
|---|---|
| Water | 700 ml |
| Sodium tetrapolyphosphonic acid | 2 g |
| Sodium sulfite | 20 g |
| Hydroquinone monosulfonate | 30 g |
| Sodium carbonate (monohydrate) | 30 g |
| 1-Phenyl-4-methyl-4-hydroxymethyl-3-pyrazolidone | 2 g |
| Potassium bromide | 2.5 g |
| Potassium thiocyanate | 1.2 g |
| Potassium iodide (0.1% solution) | 2 ml |
| Made up to 1000 ml with addition of water. | |
| Reverse solution | |
| Water | 700 ml |
| Hexasodium nitrilotrimethylenephosphonate | 3 g |
| Stannous chloride (dihydrate) | 1 g |
| p-Aminophenol | 0.1 g |
| Sodium hydroxide | 8 g |
| Glacial acetic acid | 15 ml |
| Made up to 1000 ml with addition of water. | |
| Color developing solution | |
| Sodium tetrapolyphosphonate | 2 g |
| Sodium sulfite | 7 g |
| Sodium tert-phosphate (dihydrate) | 36 g |
| Potassium bromide | 1 g |
| Potassium iodide (0.1% solution) | 90 ml |
| Sodium hydroxide | 3 g |
| Citrazinic acid | 1.5 g |
| N—Methyl-N—(β-methanesulfonamidoethyl)-3-methyl-4-aminoaniline sulfate | 11 g |
| Ethylenediamine | 3 g |
| Made up to 1000 ml with addition of water. | |
| Adjustment solution | |
| Water | 700 ml |
| Sodium sulfite | 12 g |
| Sodium ethylenediaminetetraacetate (dihydrate) | 8 g |
| Thioglycerin | 0.4 ml |
| Glacial acetic acid | 3 ml |
| Made up to 1000 ml with addition of water. | |
| Bleaching solution | |
| Sodium ethylenediaminetetraacetate (dihydrate) | 2 g |
| Iron (III) ammonium ethylenediaminetetraacetate (dihydrate) | 120.0 g |
| Ammonium bromide | 100.0 g |
| Made up to 1000 ml with addition of water. | |
| Fixing solution | |
| Water | 800 ml |
| Ammonium thiosulfate | 80.0 g |
| Sodium sulfite | 5.0 g |
| Sodium bisulfite | 5.0 g |

-continued

| | |
|---|---|
| Made up to 1000 ml with addition of water. | |
| Stabilizing solution | |
| Water | 800 ml |
| Formalin (37% by weight) | 5.0 ml |
| Konidax (produced by KONICA CORPORATION) | 5.0 ml |
| Made up to 1000 ml with addition of water. | |

TABLE 7

| Sample No. | Coupler | $D_{max}$ (red) |
|---|---|---|
| 28 (Control) | C-3 | 3.18 |
| 29 (This invention) | II-4 | 3.28 |
| 30 (This invention) | II-5 | 3.30 |
| 31 (This invention) | IV-4 | 3.45 |
| 32 (This invention) | IV-5 | 3.52 |
| 33 (This invention) | IV-6 | 3.49 |

As can be seen from the above results, the samples using the cyan coupler represented by the formula (II) or (IV) of the present invention are suitable for a reversal light-sensitive material since they are hing in $D_{max}$.

Also, as long as the evaluation with eyes of the samples photographed a color checker practically, the samples No. 29 to No. 33 of the present invention are excellent in discrimination of cyan and blue which is one of the characteristic feature of the present invention as compared with the control sample No. 28, whereby color reproducibility of green and red has been improved.

Example 7

To a silver halide emulsion prepared according to the method as described in Japanese Patent Application No. 31330/1986, that is, a core/shell silver iodobromide emulsion having a polyshell structure in which an iodide content becomes lower from a higher iodide shell at the inner portion of the grain toward the outer side, was applied a chemical sensitization according to the conventional manner, and each coating solution to which the following additives had been added was coated on a triacetylcellulose film support from the support side successively to prepare a light-sensitive color material sample No. 34 comprising 13 layers.

First layer: Halation preventive layer
a gelatin layer containing black colloidal silver.
gelatin: 2.2 g/m².
Second layer: Intermediate layer
a gelatin layer containing an emulsified dispersion of 2,5-di-t-octylhydroquinone.
gelatin: 1.2 g/m².
Third layer: Low-sensitivity red-sensitive silver halide emulsion layer
Monodispersed emulsion (emulsion V) comprising octahedral silver iodobromide containing an average iodide content of 7.84% (weight ratio) and having an average grain diameter of 0.38 μm . . . silver coated amount: 1.8 g/m²,
SD—12 . . . 6×10⁻⁵ mole per one mole of silver,
SD—13 . . . 1.0×10⁻⁵ mole per one mole of silver,
SD—14 . . . 1.0×10⁻⁵ mole per one mole of silver,
Cyan coupler (C—5) . . . 0.06 mole per one mole of silver,
Colored cyan coupler (CC—1) . . . 0.003 mole per one mole of silver,
DIR compound (D—1) . . . 0.0015 mole per one mole of silver,
DIR compound (D—2) . . . 0.002 mole per one mole of silver, and
1.4 g/m² of gelatin.
Fourth layer: High-sensitivity red-sensitive silver halide emulsion layer
Monodispersed emulsion (emulsion VI) comprising octahedral silver iodobromide containing an average iodide content of 7.37% (weight ratio) and having an average grain diameter of 0.65 μm . . . silver coated amount: 1.3 g/m²,
SD—12 . . . 3×10⁻⁵ mole per one mole of silver,
SD—13 . . . 1.0×10⁻⁵ mole per one mole of silver,
SD—14 . . . 1.0×10⁻⁵ mole per one mole of silver,
Cyan coupler (C—5) . . . 0.02 mole per one mole of silver,
Colored cyan coupler (CC—1) . . . 0.0015 mole per one mole of silver,
DIR compound (D—2) . . . 0.001 mole per one mole of silver, and
1.0 g/m² of gelatin.
Fifth layer: Intermediate layer
a gelatin layer which is the same as the second layer.
gelatin: 1.0 g/m².
Sixth layer: Low-sensitivity green-sensitive silver halide emulsion layer
Emulsion V . . . coated silver amount: 1.5 g/m²,
SD—15 . . . 2.5×10⁻⁵ mole per one mole of silver,
SD—16 . . . 1.2×10⁻⁵ mole per one mole of silver,
SD—17 . . . 1.0×10⁻⁵ mole per one mole of silver,
Magenta coupler (M—5) . . . 0.05 mole per one mole of silver,
Colored magenta coupler (CM—1) . . . 0.009 mole per one mole of silver,
DIR compound (D—1) . . . 0.0010 mole per one mole of silver,
DIR compound (D—3) . . . 0.0030 mole per one mole of silver, and
2.0 g/m² of gelatin.
Seventh layer: High-sensitivity green-sensitive silver halide emulsion layer
Emulsion VI . . . coated silver amount: 1.4 g/m²,
SD—15 . . . 1.5×10⁻⁵ mole per one mole of silver,
SD—16 . . . 1.0×10⁻⁵ mole per one mole of silver,
SD—17 . . . 7.0×10⁻⁶ mole per one mole of silver,
Magenta coupler (M—5) . . . 0.020 mole per one mole of silver,
Colored magenta coupler (CM—1) . . . 0.002 mole per one mole of silver,
DIR compound (D—3) . . . 0.0010 mole per one mole of silver, and
1.8 g/m² of gelatin.
Eighth layer: Intermediate layer
a gelatin layer which is the same as the second layer.
gelatin: 1.0 g/m².
Ninth layer: Yellow filter layer
a gelatin layer containing an emulsified dispersion of yellow collidal silver and 2,5-di-t-octylhydroquinone.
gelatin: 1.5 g/m².
Tenth layer: Low-sensitivity blue-sensitive silver halide emulsion layer
Monodispersed emulsion (Emulsion V) . . . coated silver amount: 0.9 g/m²,
SD—18 . . . 1.3×10⁻⁵ mole per one mole of silver, Yellow coupler (Y—4) ... 0.29 mole per one mole of silver, and
1.9 g/m² of gelatin.
Eleventh layer: High-sensitivity blue-sensitive silver halide emulsion layer
  Monodispersed emulsion (Emulsion VI) ... coated silver amount: 0.5 g/m²,
  SD—18 ... $1.0 \times 10^{-5}$ mole per one mole of silver,
  Yellow coupler (Y—4) ... 0.08 mole per one mole of silver,
  DIR compound (D—2) ... 0.0015 mole per one mole of silver, and
  1.6 g/m² of gelatin.
Twelfth layer: First protective layer
  a gelatin layer containing silver iodobromide (AgI: 1 mole %, average grain diameter: 0.07 μm) ... coated silver amount: 0.5 g/m²,
and ultraviolet-ray absorbers UV—2 and UV—3.
1.2 g/m² of gelatin.
Thirteenth layer: Second protective layer (Pro—2)
  a gelatin layer containing polymethyl methacrylate particles (diameter: 1.5 μm), copolymer particles of ethyl methacrylate: methyl methacrylate: methacrylic acid (avearge grain diameter: 2.5 μm),
  5 mg/m² of polydimethylsiloxane, 10 mg/m² of

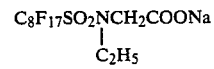

and
formalin scavenger (HS—1).
1.2 g/m² of gelatin.
In each layer, in addition to the above compositions, a gelatin hardener (H—1) and a surfactant were added thereto.

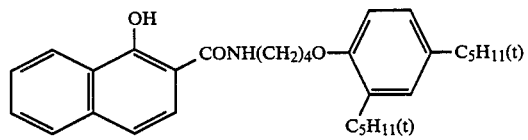

C-5

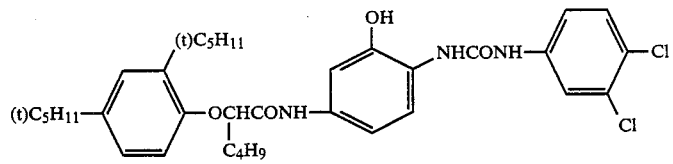

C-6

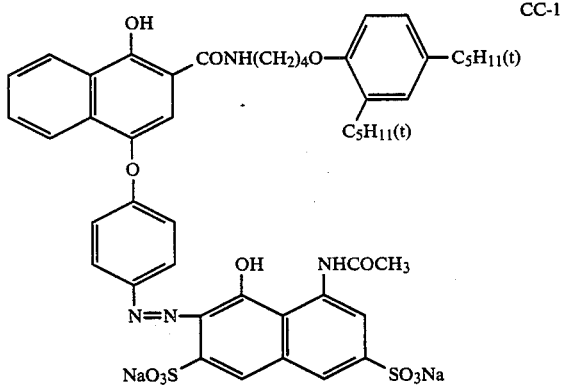

CC-1

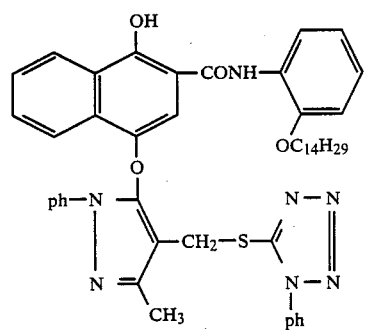

D-1

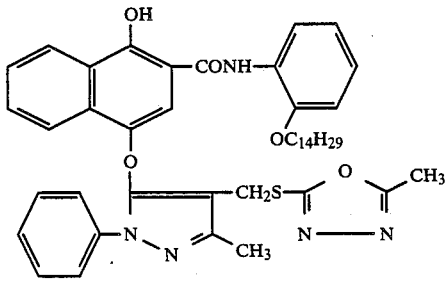

D-2

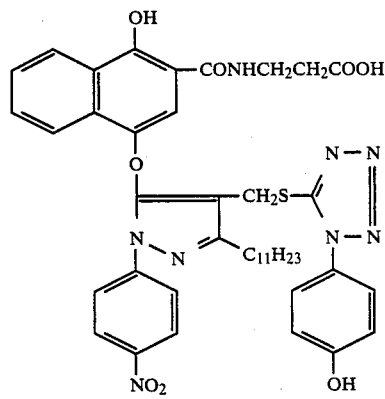

D-3

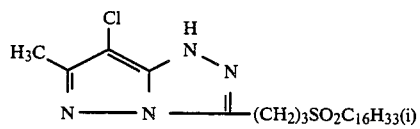 M-5
-continued
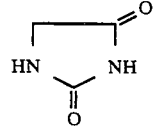 HS-1
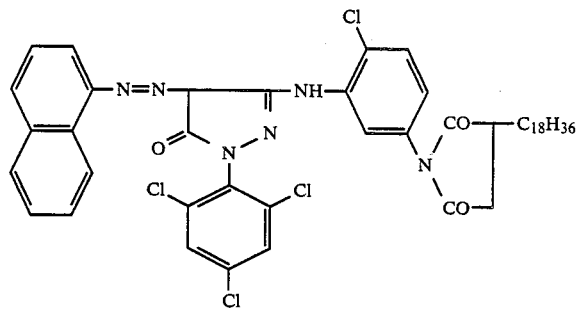 CM-1
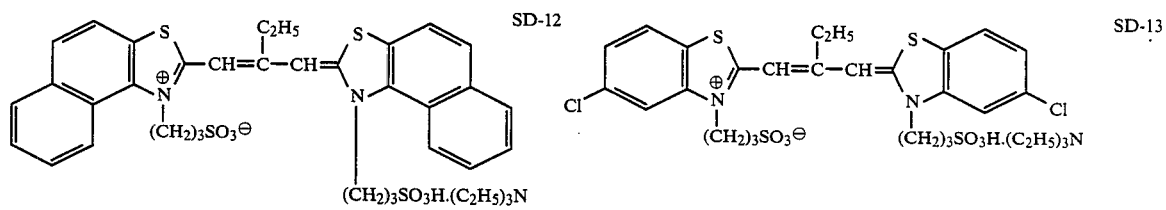
SD-12    SD-13
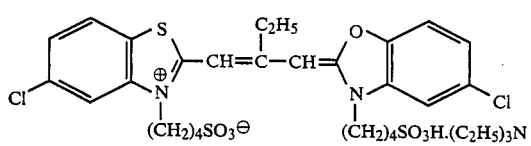 SD-14
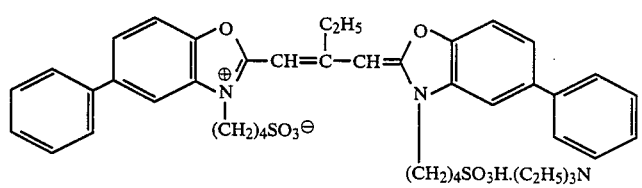 SD-15
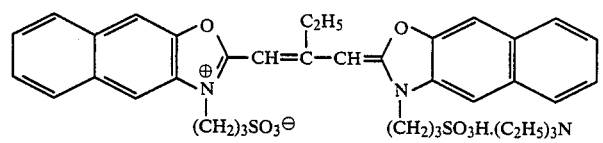 SD-16
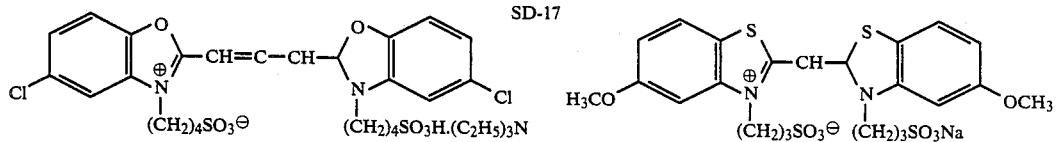
SD-17    SD-18
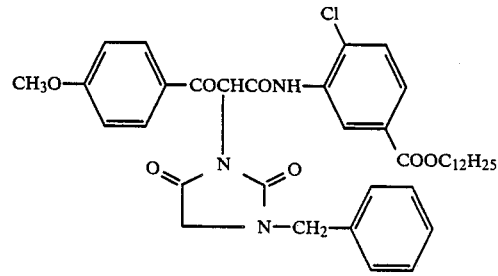 Y-4
Also, those in which the cyan couplers C—5's in the third layer and the fourth layer were replaced with those as shown in Table 8 are made samples No. 35 to 40.

Each sample thus prepared was subjected to wedge exposure with white light and was carried out the following developing processing to obtain sensitivity and fog of a panchromatic layer. The sensitivity was shown by a reverse number of an exposed dosage providing a density of fog+0.5 and shown by a relative value to the sensitivity of the sample No. 34 as 100. Also, the color reproducibility of the cyan dye was evaluated in the same manner as in Example 3. Further, with respect to the cyan image, light resistance test was carried out by a xenon fade meter for 20 days and the light resistance was shown by a density after deterioration at a density of 1.0. The results are shown in Table 8 all together.

Processing steps (38° C.)

| Color developing | 3 min 15 sec |
|---|---|
| Bleaching | 6 min 30 sec |
| Washing | 3 min 15 sec |
| Fixing | 6 min 30 sec |
| Washing | 3 min 15 sec |
| Stabilizing | 1 min 30 sec |
| Drying | |

Compositions of the processing solutions used in each of processing steps are as follows:

[Color developing solution]

| 4-Amino-3-methyl-N—ethyl-N—(β-hydroxyethyl)aniline.sulfate | 4.75 g |
|---|---|
| Anhydrous sodium sulfite | 4.25 g |
| Hydroxylamine.½sulfate | 2.0 g |
| Anhydrous potassium carbonate | 37.5 g |
| Sodium bromide | 1.3 g |
| Trisodium nitrilotriacetate (monohydrate) | 2.5 g |
| Potassium hydroxide | 1.0 g |

Made up to one liter with addition of water.

[Bleaching solution]

| Ferric ammonium ethylenediaminetetraacetate | 100.0 g |
|---|---|
| Diammonium ethylenediaminetetraacetate | 10.0 g |
| Ammonium bromide | 150.0 g |
| Glacial acetic acid | 10.0 ml |

Made up to one liter with addition of water and adjusted to pH=6.0 with aqueous ammonia.

[Fixing solution]

| Ammonium thiosulfate | 175.0 g |
|---|---|
| Anhydrous sodium sulfite | 8.5 g |
| Sodium metasulfite | 2.3 g |

Made up to one liter with addition of water and adjusted to pH=6.0 with acetic acid.

[Stabilizing solution]

| Formalin (37% aqueous solution) | 1.5 ml |
|---|---|
| Konidax (produced by KONICA CORPORATION) | 7.5 ml |

Made up to one liter with addition of water.

TABLE 8

| Sample No. | Coupler | Sensi-* tivity | Color reproducibility (%) | Light resistance | max (nm) |
|---|---|---|---|---|---|
| 34 (Control) | C-5 | 100 | 75 | 0.75 | 700 |
| 35 (Control) | C-6 | 78 | 97 | 0.78 | 692 |
| 36 (Control) | C-3 | 69 | 95 | 0.80 | 668 |
| 37 (This invention) | III-2 | 102 | 96 | 0.94 | 700 |
| 38 (This invention) | III-4 | 105 | 97 | 0.95 | 695 |
| 39 (This invention) | III-5 | 103 | 98 | 0.92 | 703 |
| 40 (This invention) | III-7 | 159 | 99 | 0.93 | 703 |

As seen from the results of Table 8, it can be understood that the cyan couplers of the formula (III) of the present invention have high sensitivity and are excellent in color reproducibility and light resistance. Heretofore, a naphthol type cyan coupler such as C—5 has conventionally been employed for a color negative film in an aspect of wavelength but a coupler of C—6 type has also been employed since the former is bad in color reproducibility.

On the other hand, since the C—6 type coupler has become longer wavelength due to their association so that absorption wavelength is broad and yet main wavelength thereof is slightly a short wave, and also there is a problem in light resistance.

The cyan coupler C—3 which has partially similar structure to that of the present invention is extremely a short wave in absorption wavelength as in a phenol type cyan coupler which is conventionally known, thus it is clear that it is basically different from the coupler of the present invention.

That is, it can be understood from the present Examples that the coupler represented by the formula (III) of the present invention is a epoch-making cyan coupler which can solve various problems as mentioned above.

We claim:

1. A light-sensitive silver halide color photographic material having at least one silver halide emulsion layer on a support, characterized in that at least one layer of said silver halide emulsion layer contains at least one cyan coupler represented by the formula (I) shown below:

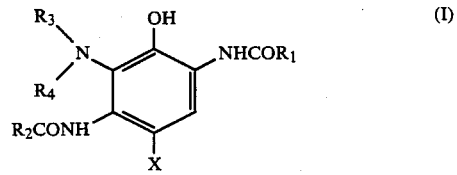

wherein $R_1$ and $R_2$ each represent an alkyl group, an aryl group, a heterocyclic group, a dialkylamino group, an anilino group, an alkoxy group or an aryloxy group; $R_3$ represents a hydrogen atom or an alkyl group; $R_4$ represents a hydrogen atom, an alkyl group, an aryl group, a $R_5CO$— group or a $R_5SO_2$— group; provided that $R_3$ and $R_4$ cannot be hydrogen atoms at the same time; $R_5$ represents a hydrogen atom, an alkyl group, an aryl group, a dialkylamino group, an anilino group, an alkoxy group or an aryloxy group; and X represents a hydrogen atom or an eliminatable group through the reaction with the oxidized product of a color developing agent.

2. The light-sensitive silver halide color photographic material according to claim 1, wherein the $R_1$ or $R_2$ is selected from the group consisting of groups of methyl, ethyl, iso-propyl, t-butyl, cyclohexyl, undecyl, trifluoromethyl, trichloromethyl, perfluoropropyl, 2-methoxyethyl, hyroxymethyl, benzyl, phenethyl, 3-(2,5-di-t-amylphenoxy)propyl, 1-(4-butanesulfonamidophenoxy)tridecyl, 1-(2,4,6-trichlorophenoxy)-undecyl; unsubstituted aryl, substituted-aryl substituted with halogen atoms or with each groups of alkyl, aryl, heterocyclic, alkoxy, aryloxy, acyl, ester, amide, imide, ureido, sulfonyl, alkoxycarbonyl, aryloxycarbonyl, hydroxy, carboxy, sulfo, cyano and nitro; 2-furyl, 2-imidazolyl, 2-thienyl, 2-pyridyl, 6-quinolyl; dimethylamino, diethylamino, methylbutylamino; anilino substituted with halogen atoms, alkyl, alkoxy, amide, sulfonamide, cyano or nitro; methoxy, ethoxy, butoxy, octyloxy and dodecyloxy.

3. The light-sensitive silver halide color photographic material according to claim 1, wherein the alkyl group represented by $R_3$ or $R_4$ is a substituted or unsubstituted alkyl group having 1 to 22 carbon atoms.

4. The light-sensitive silver halide color photographic material according to claim 1, wherein $R_3$ is a hydrogen atom or a lower alkyl group and $R_4$ is an alkylcarbonyl or arylcarbonyl group, an alkylsulfonyl or arylsulfonyl group.

5. The light-sensitive silver halide color photographic material according to claim 1, wherein X is a split-off group.

6. The light-sensitive silver halide color photographic material according to claim 1, wherein the compound represented by the formula (I) is 2-pentafluorobenzamido-4-chloro-5-{2-(2,4-di-t-amylphenoxy)-3-methylbutaneamido}-6-acetamidophenol.

7. The light-sensitive silver halide color photographic material according to claim 1, wherein an amount of the cyan coupler represented by the formula (I) in a red-sensitive emulsion layer is in the range of $2 \times 10^{-3}$ to $8 \times 10^{-1}$ mole per one mole of silver halide.

8. A light-sensitive silver halide color photographic material having at least one silver halide emulsion layer on a support, characterized in that at least one layer of said silver halide emulsion layer contains at least one cyan coupler represented by the following formula (II):

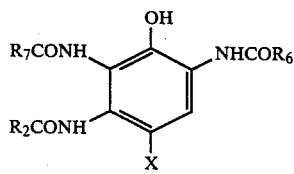

wherein $R_2$ represents an alkyl group, an aryl group, a heterocyclic group, a dialkylamino group, an anilino group, an alkoxy group or an aryloxy group; X represents a hydrogen atom or an eliminatable group through the reaction with the oxidized product of a color developing agent;

$R_6$ represents an alkyl group substituted by at least one halogen atom; and $R_7$ represents a substituted or unsubstituted amino group, an alkoxy group or an aryloxy group.

9. The light-sensitive silver halide color photographic material according to claim 1, wherein said cyan coupler is the compound represented by the following formula (III):

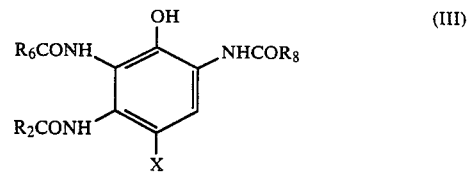

wherein $R_2$ and X have the same meanings as $R_2$ and X in claim 1, respectively; $R_6$ represents an alkyl group substituted by at least one halogen atom; and $R_8$ represents a substituted or unsubstituted phenyl group.

10. A light-sensitive silver halide color photographic material having at least one silver halide emulsion layer on a support, characterized in that at least one layer of said silver halide emulsion layer contains at least one cyan coupler represented by the following formula (IV):

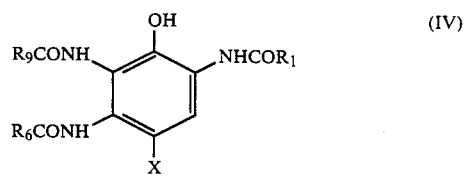

wherein $R_1$ represents an alkyl group, an aryl group, a heterocyclic group, a dialkylamino group, an anilino group, an alkoxy group or an aryloxy group; X represents a hydrogen atom or an eliminatable group through the reaction with the oxidized product of a color developing agent; $R_6$ represents an alkyl group substituted by at least one halogen atom; and $R_9$ represents a substituted or unsubstituted amino group, alkoxy group, alkyl group or aryl group.

11. The light-sensitive silver halide color photographic material according to claim 1, wherein the compound represented by the formula (I) is used by dissolving in a high boiling point organic solvent having a boiling point of 150° C. or higher and/or a low boiling point organic solvent having a boiling point of 30° to 150° C. and then dispersing in a hydrophilic colloid.

12. The light-sensitive silver halide color photographic material according to claim 1, wherein silver halide grains used in at least one of the silver halide emulsion layers are silver chloride, silver chlorobromide or silver iodobromide containing silver chloride.

13. The light-sensitive silver halide color photographic material according to claim 12, wherein said silver halide grains are silver halide grains for rapid processing containing 90 mole % or more of silver chloride.

14. The light-sensitive silver halide color photographic material according to claim 13, wherein said silver halide grains for rapid processing contain 90 mole % or more of silver chloride, with the silver bromide content of 5 mole % or less and the silver iodide content of 0.5 mole % or less.

15. The light-sensitive silver halide color photographic material according to claim 8, wherein $R_2$ is selected from the group consisting of methyl, ethyl, iso-propyl, t-butyl, cyclohexyl, undecyl, trifluoromethyl, trichloromethyl, perfluoropropyl, 2-methoxyethyl, hydroxymethyl, benzyl, phenethyl, 3-(2,5-di-t-amylphenoxy)-propyl, 1-(4-butanesulfonamidophenoxyl)tridecyl, 1-(2,4,6-trichlorophenoxy)-undecyl; unsubstituted aryl, substituted-aryl substituted with halogen atoms or with a group selected from the group consisting of alkyl, aryl, heterocyclic, alkoxy, aryloxy, acyl, ester, amide, imide, ureido, sulfonyl, alkoxycarbonyl, aryloxycrbonyl, hydroxy, carboxy, sulfo, cyano and nitro; 2-furyl, 2-imidazolyl, 2-thienyl, 2-pyridyl, 6-quinolyl; dimethylamino, diethylamino, methylbutylamino; anilino substituted with halogen atoms, alkyl, alkoxy, amide, sulfonamide, cyano or nitro; methoxy, ethoxy, butoxy, octyloxy and dodecyloxy.

16. The light-sensitive silver halide photographic material according to claim 15 wherein X is a hydrogen atom, a chlorine atom, a substituted or unsubstituted alkoxy group or an aryloxy group.

17. The light-sensitive silver halide photographic material according to claim 16 wherein X is a chlorine atom, a substituted alkoxy group or a substituted aryloxy group.

18. The light-sensitive silver halide color photographic material according to claim 10, wherein $R_1$ is selected from the group consisting of methyl, ethyl, iso-propyl, t-butyl, cyclohexyl, undecyl, trifluoromethyl, trichloromethyl, perfluoropropyl, 2-methoxyethyl, hydroxymethyl, benzyl, phenethyl, 3-(2,5-di-t-amylphenoxy)-propyl, 1-(4-butanesulfonamidophenoxyl)tridecyl, 1-(2,4,6-trichlorophenoxy)-undecyl; unsubstituted aryl, substituted-aryl substituted with halogen atoms or with a group selected from the group consisting of alkyl, aryl, heterocyclic, alkoxy, aryloxy, acyl, ester, amide, imide, ureido, sulfonyl, alkoxycarbonyl, aryloxycrbonyl, hydroxy, carboxy, sulfo, cyano and nitro; 2-furyl, 2-imidazolyl, 2-thienyl, 2-pyridyl, 6-quinolyl; dimethylamino, diethylamino, methylbutylamino; anilino substituted with halogen atoms, alkyl, alkoxy, amide, sulfonamide, cyano or nitro; methoxy, ethoxy, butoxy, octyloxy and dodecyloxy.

19. The light-sensitive silver halide photographic material according to claim 18 wherein X is a hydrogen atom, a chlorine atom, a substituted or unsubstituted alkoxy group or an aryloxy group.

20. The light-sensitive silver halide photographic material according to claim 19 wherein X is a chlorine atom, a substituted alkoxy group or a substituted aryloxy group.

21. The light-sensitive silver halide photographic material according to claim 2 wherein X is a hydrogen atom, a chlorine atom, a substituted or unsubstituted alkoxy group or an aryloxy group.

22. The light-sensitive silver halide photographic material according to claim 21 wherein X is a chlorine atom, a substituted alkoxy group or a substituted aryloxy group.

* * * * *